United States Patent
Jiang et al.

(10) Patent No.: US 10,889,637 B2
(45) Date of Patent: Jan. 12, 2021

(54) METHODS OF TREATING AN OSTEOLYTIC TUMOR AND SPINAL CORD INJURY BY ADMINISTERING CONNEXIN (CX) 43 HEMICHANNEL-BINDING ANTIBODIES

(71) Applicant: THE BOARD OF REGENTS OF THE UNIVERSITY OF TEXAS SYSTEM, Austin, TX (US)

(72) Inventors: Jean X. Jiang, Helotes, TX (US); Zhiqiang An, Houston, TX (US); Ningyan Zhang, Houston, TX (US); Wei Xiong, Houston, TX (US); Manuel A. Riquelme, San Antonio, TX (US); Sumin Gu, San Antonio, TX (US); Naomi Ledene Sayre, San Antonio, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/078,990

(22) PCT Filed: Feb. 27, 2017

(86) PCT No.: PCT/US2017/019605
§ 371 (c)(1),
(2) Date: Aug. 22, 2018

(87) PCT Pub. No.: WO2017/147561
PCT Pub. Date: Aug. 31, 2017

(65) Prior Publication Data
US 2019/0359696 A1    Nov. 28, 2019

Related U.S. Application Data

(60) Provisional application No. 62/300,492, filed on Feb. 26, 2016.

(51) Int. Cl.
| | | |
|---|---|---|
| C07K 16/18 | (2006.01) | |
| A61P 25/28 | (2006.01) | |
| A61P 19/10 | (2006.01) | |
| A61K 39/395 | (2006.01) | |
| A61P 35/00 | (2006.01) | |

(52) U.S. Cl.
CPC ............ *C07K 16/18* (2013.01); *A61K 39/395* (2013.01); *A61P 19/10* (2018.01); *A61P 25/28* (2018.01); *A61P 35/00* (2018.01); *C07K 2317/24* (2013.01); *C07K 2317/75* (2013.01); *C07K 2317/76* (2013.01)

(58) Field of Classification Search
CPC .......................... C07K 16/18; C07K 2317/24; C07K 2317/75; C07K 2317/76; A61P 19/10; A61P 25/28; A61P 31/00; A61K 2039/505
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,196,265 A | 4/1980 | Koprowski et al. |
| 4,275,149 A | 6/1981 | Litman et al. |
| 4,277,437 A | 7/1981 | Maggio |
| 4,366,241 A | 12/1982 | Tom et al. |
| 4,469,797 A | 9/1984 | Albarella |
| 4,472,509 A | 9/1984 | Gansow et al. |
| 4,606,855 A | 8/1986 | Deutsch et al. |
| 4,703,003 A | 10/1987 | Struck |
| 4,742,159 A | 5/1988 | Batz et al. |
| 4,767,720 A | 8/1988 | Lingwood |
| 4,816,567 A | 3/1989 | Cabilly et al. |
| 4,867,973 A | 9/1989 | Goers et al. |
| 4,870,287 A | 9/1989 | Cole et al. |
| 4,938,948 A | 7/1990 | Ring et al. |
| 4,946,778 A | 8/1990 | Ladner et al. |
| 5,021,236 A | 6/1991 | Gries et al. |
| 5,091,513 A | 2/1992 | Huston et al. |
| 5,164,296 A | 11/1992 | Blaustein et al. |
| 5,196,066 A | 3/1993 | Kusuda et al. |
| 5,223,409 A | 6/1993 | Ladner et al. |
| 5,403,484 A | 4/1995 | Ladner et al. |
| 5,420,253 A | 5/1995 | Emery et al. |

(Continued)

FOREIGN PATENT DOCUMENTS

| | | |
|---|---|---|
| CN | 1638790 A | 7/2005 |
| EP | 2700652 A1 | 2/2014 |

(Continued)

OTHER PUBLICATIONS

Kar R, et al. (Jul. 2013) J Bone Miner Res. 28(7):1611-1621 (doi: 10.1002/jbmr.1917).*

(Continued)

*Primary Examiner* — Robert S Landsman
(74) *Attorney, Agent, or Firm* — Ballard Spahr LLP

(57) ABSTRACT

Antibodies that bind to connexin 43 hemichannels and inhibit, or activate, channel opening are provided. In certain aspects, methods for detecting or treating cancers with antibodies that activate Cx43 channel opening are also provided. Likewise, methods for treating inflammatory diseases (e.g., osteoarthritis) and neurological injuries (e.g., spinal cord injury) with antibodies that inhibit Cx43 channel opening are provided.

10 Claims, 14 Drawing Sheets
Specification includes a Sequence Listing.

(56) References Cited

U.S. PATENT DOCUMENTS

| | | | |
|---|---|---|---|
| 5,565,332 | A | 10/1996 | Hoogenboom et al. |
| 5,571,698 | A | 11/1996 | Ladner et al. |
| 5,627,052 | A | 5/1997 | Schrader |
| 5,656,434 | A | 8/1997 | Terano et al. |
| 5,739,169 | A | 4/1998 | Ocain et al. |
| 5,760,395 | A | 6/1998 | Johnstone |
| 5,770,376 | A | 6/1998 | Bagrov |
| 5,789,208 | A | 8/1998 | Sharon |
| 5,801,005 | A | 9/1998 | Cheever et al. |
| 5,821,337 | A | 10/1998 | Carter et al. |
| 5,824,311 | A | 10/1998 | Greene et al. |
| 5,830,880 | A | 11/1998 | Sedlacek et al. |
| 5,844,091 | A | 12/1998 | Blaustein et al. |
| 5,846,945 | A | 12/1998 | McCormick |
| 5,858,657 | A | 1/1999 | Winter et al. |
| 5,861,155 | A | 1/1999 | Lin |
| 5,871,907 | A | 2/1999 | Winter et al. |
| 5,969,108 | A | 10/1999 | McCafferty et al. |
| 6,054,297 | A | 4/2000 | Carter et al. |
| 6,165,464 | A | 12/2000 | Hudziak et al. |
| 6,365,157 | B2 | 4/2002 | Rockwell et al. |
| 6,406,867 | B1 | 6/2002 | Yu et al. |
| 6,492,425 | B1 | 12/2002 | Callahan et al. |
| 6,709,659 | B1 | 3/2004 | Lok et al. |
| 6,709,873 | B1 | 3/2004 | Yatscoff et al. |
| 6,753,407 | B2 | 6/2004 | Noga et al. |
| 6,814,965 | B2 | 11/2004 | Gao et al. |
| 6,849,259 | B2 | 2/2005 | Haurum et al. |
| 6,861,572 | B1 | 3/2005 | Etches et al. |
| 6,875,434 | B1 | 4/2005 | Schenk |
| 6,881,557 | B2 | 4/2005 | Foote |
| 6,891,024 | B2 | 5/2005 | Marsh |
| 6,946,546 | B2 | 9/2005 | Vaughan et al. |
| 7,153,822 | B2 | 12/2006 | Jensen et al. |
| 2002/0172677 | A1 | 11/2002 | Lahn et al. |
| 2004/0092429 | A1 | 5/2004 | Jensen et al. |
| 2004/0126828 | A1 | 7/2004 | Karumanchi et al. |
| 2005/0214860 | A1 | 9/2005 | Zhu et al. |
| 2005/0260623 | A1 | 11/2005 | Trosko et al. |
| 2007/0042964 | A1 | 2/2007 | Jensen et al. |
| 2009/0142295 | A1 | 6/2009 | Becker |
| 2011/0065770 | A1* | 3/2011 | Becker ............... C12N 15/111 514/44 A |
| 2011/0243964 | A1 | 10/2011 | Duft |
| 2014/0371297 | A1 | 12/2014 | Laux et al. |

FOREIGN PATENT DOCUMENTS

| | | |
|---|---|---|
| RU | 2408728 | 1/2011 |
| RU | 2457862 | 8/2012 |
| WO | WO-2003/063891 A1 | 8/2003 |
| WO | WO-2005/116236 A1 | 12/2005 |
| WO | WO-2006/134494 A2 | 12/2006 |
| WO | WO-2010/072691 A1 | 7/2010 |
| WO | WO-2013/163423 A1 | 10/2013 |
| WO | WO-2015/027120 A1 | 2/2015 |
| WO | WO-2017/147561 A1 | 8/2017 |

OTHER PUBLICATIONS

Lima F, et al. (Jun. 2009) Mol Biol Cell. 20(11):2697-2708 (doi: 10.1091/mbc.E08-10-1079).*

Colman, PM " Effects of amino acid sequence changes on antibody-antigen interactions",(1994) Research in Immunology, Elsevier, NY, 145(1):33-36.

Edwards, BM et al. "The remarkable flexibility of the human antibody repertoire; isolation of over one thousand different antibodies to a single protein, BLyS", (2003) J. Mol. Biol. 334:103-118.

Lloyd, C et al. "Modelling the human immune response: performance of a 1011 human antibody repertoire against a broad panel of therapeutically relevant antigens" (2009) Protein Engineering, Design & Selection. 22(3):159-168.

Rudikoff, Set al. "Single amino acid substitution altering antigen-binding specificity", (1982) Proc. Natl. Acad. Sci. USA, 79:1979-1983.

Paul, WE (1993) Fundamental Immunology, 3rd ed. Raven Press, NY, Chap. 9, pp. 292-295.

Non Final Rejection dated Jun. 17, 2019 by the USPTO for U.S. Appl. No. 15/891,802, which was filed Feb. 8, 2018 and published as US 2018-0179278 A1 on Jun. 28, 2018 (Inventor—Jean X. Jiang) (12 pages).

Baklaushev et al., Treatment of glioma by cisplatin-loaded nanogels conjugated with monoclonal antibodies against Cx43 and BSAT1. Drug Deliv. 2015; 22(3):276-85.

Calias et al., Intrathecal delivery of protein therapeutics to the brain: A critical assessment. Pharmacol Thera. 2014; 144:114-22.

Chanson et al., Gap junctional communication in tissue inflammation and repair. Biochim Biophys Acta. 2005; 1711:197-207.

Cochrane et al., Monoclonal antibodies against the connexin43-interacting protein CIP85. Hybridoma (Larchmt). 2009; 28(5):355-61.

Cronin et al., Blocking connexin43 expression reduces inflammation and improves functional recovery after spinal cord injury. Mol Cell Neurosci. 2008; 39(2):152-60.

Dodev, T.S. et al., A Tool Kit for rapid Cloning an Expression of Recombinant Antibodies. Sci Rep. 2014; 4:5885.

Huang et al., Critical role of connexin 43 in secondary expansion of traumatic spinal cord injury. J Neurosci. 2012; 32(10):3333-8.

Ilversaro, J. et al., Connexin-mimetic Peptide Gap 27 Decreases Osteoclastic Activity. BMC Musculoskelet Disord. 2001; 2:10.

Kielian, Glial connexins and gap junctions in CNS inflammation and disease. J Neurochem. 2008; 106(3):1000-16.

Kolstelny et al., Formation of a Bispecific Antibody by the Use of Leucine Zippers. J Immunol. 1992; 148(5):1547-53.

Labome, Cx43 Antibody. Cx43 Antibody | Antibody Review Based on Formal Publications. Labome, 2017. Retrieved from Internet: https://www.labome.com/review/gene/human!Cx43-antibody.html, Accessed Jun. 14, 2017 (36 pages).

Lamiche, Influence of connexin 43 on prostatic cancer cells phenotype and on bone metastases development. Universite de Poitiers. Dissertation, pp. 142-189 (2011). Retrieved from Internet: <http://www.opengrey.eu/item/display/10068/887237> on Dec. 5, 2014. (English abstract of French publication).

Maknojia et al., Cx43 function blocking antibody improves outcome and reduces secondary expansion in traumatic spinal cord injury (SCI). AANS, Abstract, Article ID: AA-35194, May 1, 2016.

Nagy et al., Selective monoclonal antibody recognition and cellular localization of an unphosphorylated form of connexin43. Exp Cell Res. 1997; 236(1):127-36.

Niger et al., Interleukin-1 β increases gap junctional communication among synovial fibroblasts via the extracellular-signal-regulated kinase pathway. Biol Cell. 2009; 102(1):37-49.

Orellana et al., Amyloid ~-induced death in neurons involves glial and neuronal hemichannels. J Neurosci. 2011; 31(13):4962-77.

Oviedo-Orta and Evans, Gap junctions and connexin-mediated communication in the immune system. Biochim Biophys Acta. 2004; 1662:102-12.

Perez-Armendariz, E.M. et al., Connexin43 is Expressed in Mouse Fetal Ovary. Anat Rec A. 2003; 271A:360-7.

Plotkin, L.I., Connexin 43 Hemichannels and Intracellular Signaling in Bone Cells. Front Physiol. 2014; 5:131 (8 pages).

Ren et al., Occludin and connexin 43 expression contribute to the pathogenesis of traumatic brain edema. Neural Regen Res. 2013; 8(29):2703-12.

Riquelme et al., Antibodies targeting extracellular domain of connexins for studies of hemichannels. Neuropharmacology. 2013; 75:525-32.

Riquelme, M.A. et al., The ATP Required for Potentiation of Skeletal Muscle Contraction is Released via Pannexin Hemichannels. Neuropharmacology. 2013; 75:594-603.

Siller-Jackson et al., Adaptation of connexin 43-hemichannel prostaglandin release to mechanical loading. J Biol Chem. 2008; 283:26374-82.

(56) References Cited

OTHER PUBLICATIONS

Songsivilai, S. and Lachmann, P.J., Bispecific Antibody: a Tool for Diagnosis and Treatment of Disease. Clin Exp Immunol. 1990; 79:315-21.
Ward, E.S. et al., Binding Activities of a Repertoire of Single Immunoglobulin Variable Domains Secreted from *Escherichia coli.* Nature. 1989; 341(6242):544-6.
Wong et al., the role of gap junctions in inflammatory and neoplastic disorders (Review). Intl J Mol Med. 2017; 39:498-506.
Yusubalieva et al., Antitumor effects of monoclonal antibodies to connexin 43 extracellular fragment in induced low-differentiated glioma. Cell Technol Biol Med. 2012; 1:163-9.
Zhou et al., Osteocytic connexin hemichannels suppress breast cancer growth and bone metastasis. Oncogene. 2016; 35(43):5597-607.
Extended European Search Report dated Mar. 29, 2017 by the European Patent Office for Patent Application No. 14838354.0, which was filed on Aug. 21, 2014 and published as EP 3036005 on Jun. 29, 2016 (Inventor—Jiang et al.; Applicant—Applicant—Board of Regents, Univ. of Texas System) (7 pages).
International Search Report and Written Opinion dated Dec. 19, 2014 by the International Searching Authority for Patent Application No. PCT/US2014/052206, which was filed on Aug. 21, 2014 and published as WO 2015/027120 on Feb. 26, 2015 (Inventor—Jiang et al.; Applicant—Applicant—Board of Regents, Univ. of Texas System) (9 pages).
International Preliminary Report on Patentability dated Feb. 23, 2016 by the International Searching Authority for Patent Application No. PCT/US2014/052206, which was filed on Aug. 21, 2014 and published as WO 2015/027120 on Feb. 26, 2015 (Inventor—Jiang et al.; Applicant—Applicant—Board of Regents, Univ. of Texas System) (7 pages).
Preliminary Amendment filed on Feb. 19, 2016 with the U.S. Patent and Trademark Office for U.S. Appl. No. 14/912,986, which was filed on Feb. 19, 2016 now U.S. Pat. No. 9,914,775 on Mar. 13, 2018 (Inventor—Jiang et al.; Applicant—Board of Regents, Univ. of Texas System) (3 pages).
Preliminary Amendment filed on Aug. 4, 2016 with the U.S. Patent and Trademark Office for U.S. Appl. No. 14/912,986, which was filed on Feb. 19, 2016 now U.S. Pat. No. 9,914,775 on Mar. 13, 2018 (Inventor—Jiang et al.; Applicant—Board of Regents, Univ. of Texas System) (5 pages).
Restriction Requirement dated Nov. 9, 2016 by the U.S. Patent and Trademark Office for U.S. Appl. No. 14/912,986, filed Feb. 19, 2016 now U.S. Pat. No. 9,914,775 on Mar. 13, 2018 (Inventor—Jiang et al.; Applicant- Board of Regents, Univ. of Texas System) (6 pages).
Response to Restriction Requirement filed on Mar. 9, 2017 with the U.S. Patent and Trademark Office for U.S. Appl. No. 14/912,986, which was filed on Feb. 19, 2016 and now U.S. Pat. No. 9,914,775 on Mar. 13, 2018 (Inventor—Jiang et al.; Applicant—Board of Regents, Univ. of Texas System) (5 pages).
Non-Final Office Action dated Apr. 5, 2017 by the U.S. Patent and Trademark Office for U.S. Appl. No. 14/912,986, which was filed on Feb. 19, 2016 and now U.S. Pat. No. 9,914,775 on Mar. 13, 2018 (Inventor—Jiang et al.; Applicant—Board of Regents, Univ. of Texas System) (9 pages).
Response to Non-Final Office Action filed on Oct. 5, 2017 with the U.S. Patent and Trademark Office for U.S. Appl. No. 14/912,986, which was filed on Feb. 19, 2016 now U.S. Pat. No. 9,914,775 on Mar. 13, 2018 (Inventor—Jiang et al.; Applicant—Board of Regents, Univ. of Texas System) (94 pages).
Notice of Allowance dated Oct. 23, 2017 by the U.S. Patent and Trademark Office for U.S. Appl. No. 14/912,986, which was filed on Feb. 19, 2016 and now U.S. Pat. No. 9,914,775 on Mar. 13, 2018 (Inventor—Jiang et al.; Applicant—Board of Regents, Univ. of Texas System) (7 pages).
Notice of Allowance dated Nov. 1, 2017 by the U.S. Patent and Trademark Office for U.S. Appl. No. 14/912,986, which was filed on Feb. 19, 2016 and now U.S. Pat. No. 9,914,775 on Mar. 13, 2018 (Inventor—Jiang et al.; Applicant—Board of Regents, Univ. of Texas System) (4 pages).
Notice of Allowance dated Dec. 12, 2017 by the U.S. Patent and Trademark Office for U.S. Appl. No. 14/912,986, which was filed on Feb. 19, 2016 and now U.S. Pat. No. 9,914,775 on Mar. 13, 2018 (Inventor—Jiang et al.; Applicant—Board of Regents, Univ. of Texas System) (4 pages).
Issue Notification issued on Feb. 21, 2018 by the U.S. Patent and Trademark Office for U.S. Appl. No. 14/912,986, which was filed on Feb. 19, 2016 and now U.S. Pat. No. 9,914,775 on Mar. 13, 2018 (Inventor—Jiang et al.; Applicant—Board of Regents, Univ. of Texas System) (1 page).
Preliminary Amendment filed on Feb. 8, 2018 with the U.S. Patent and Trademark Office for U.S. Appl. No. 15/891,802, which was filed on Feb. 8, 2018 and published as US 2018/0179278 on Jun. 28, 2018 (Inventor—Jiang et al.; Applicant—Board of Regents, Univ. of Texas System) (3 pages).
International Search Report and Written Opinion dated Jul. 17, 2017 by the International Searching Authority for Patent Application No. PCT/US2017/019605, which was filed on Feb. 27, 2017 and published as WO 2017/147561 on Aug. 31, 2017 (Inventor—Jiang et al.; Applicant—Board of Regents, Univ. of Texas System) (16 pages).
International Preliminary Report on Patentability dated Aug. 28, 2018 by the International Searching Authority for Patent Application No. PCT/US2017/019605, which was filed on Feb. 27, 2017 and published as WO 2017/147561 on Aug. 31, 2017 (Inventor—Jiang et al.; Applicant—Board of Regents, Univ. of Texas System) (11 pages).
European Search Report and Written Opinion dated Aug. 28, 2019 by the European Patent Office for EP Application No. 17757405.0, filed on Feb. 27, 2017 and published as EP 3419998 on Jan. 2, 2019 (Applicant—The Board of Regents of the University of Texas System) (10 Pages).
Li YY, Zhang B, Han F, Liu ZY and Jin FG. Progress on Connexin43. Progress in Modern Biomedicine 2012, 12: 3731-3733.
Office Action dated Dec. 4, 2019 by the SIPO for CN Application No. 201480056187.5, filed on Aug. 21, 2014 and published as CN 106659909 on May 10, 2017 (Applicant—Board of Regents of the University of Texas System)(Original-5 Pages // Translation-8 Pages).

* cited by examiner

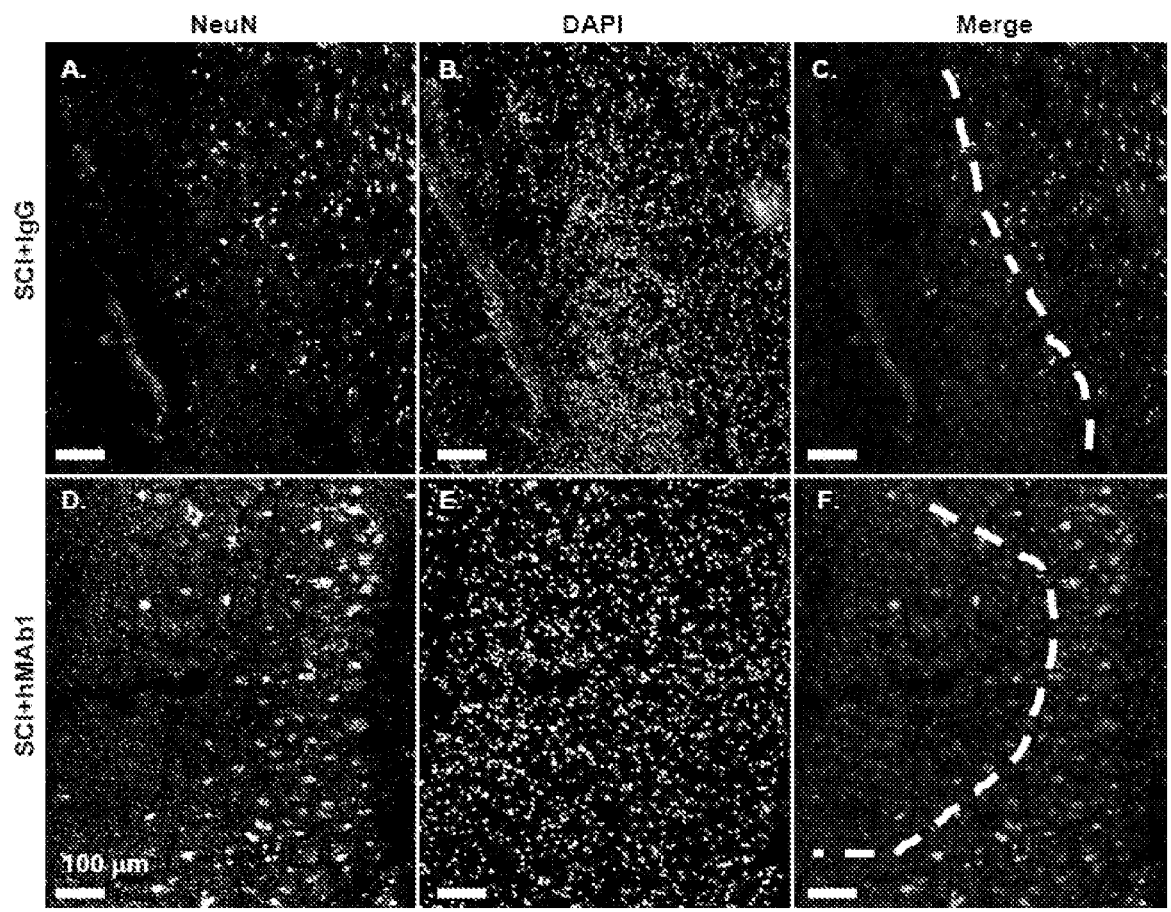
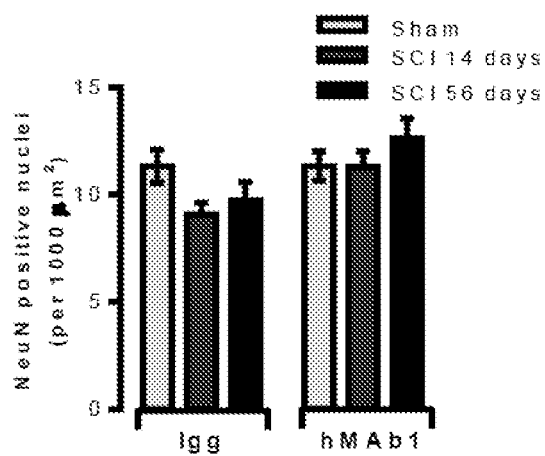
FIGS. 7A-7G

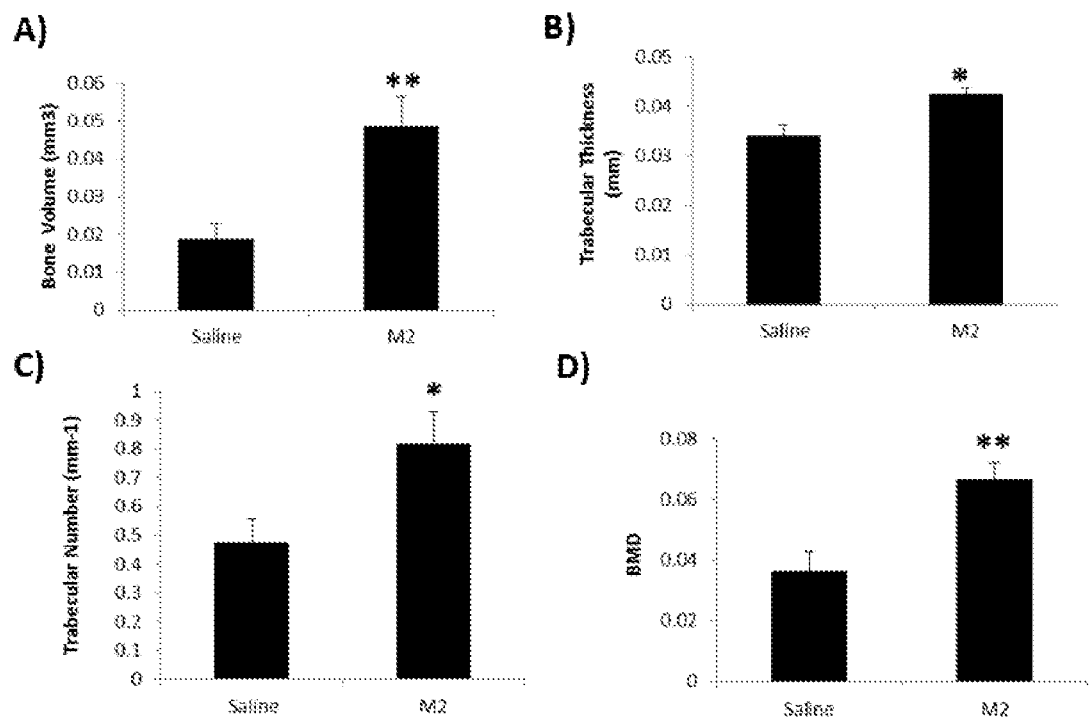
FIG. 17A-D
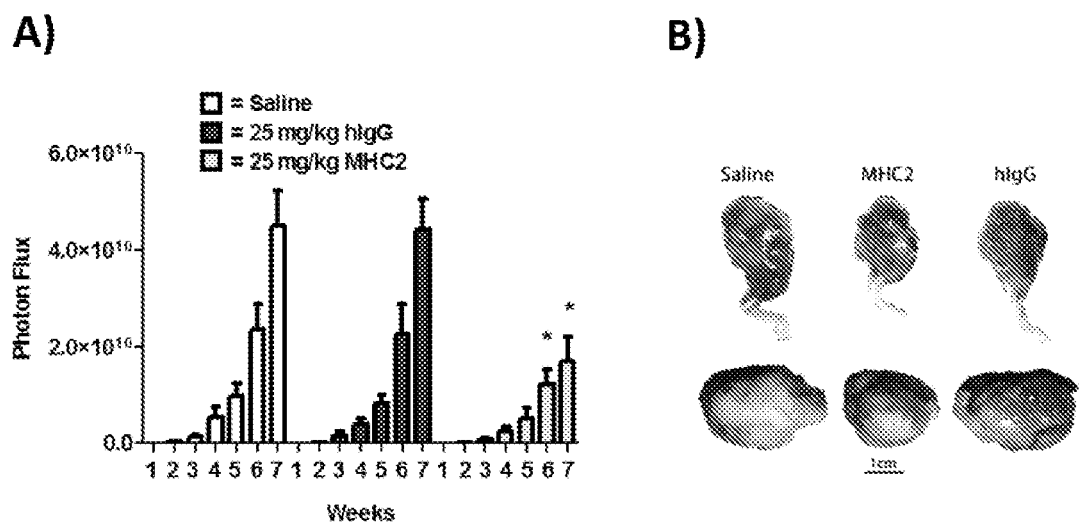
FIG. 18A-B

METHODS OF TREATING AN OSTEOLYTIC TUMOR AND SPINAL CORD INJURY BY ADMINISTERING CONNEXIN (CX) 43 HEMICHANNEL-BINDING ANTIBODIES

CROSS REFERENCE TO RELATED PATENT APPLICATIONS

This application claims the benefit of priority under 35 U.S.C. § 371 of International Application No. PCT/US2017/009605, filed on Feb. 27, 2017, which claims priority to U.S. Provisional Application No. 62/300,492, filed Feb. 26, 2016. The content of these earlier filed applications is hereby incorporated by reference.

INCORPORATION OF THE SEQUENCE LISTING

The sequence listing submitted herewith as a text file named "21105_0052_SL", created on Aug. 22, 2018 and having a size of 28,672 bytes is herein incorporated by reference in its entirety pursuant to 37 C.F.R. § 1.52(e)(5).

BACKGROUND

1. Field of the Invention

The present invention, in some embodiments, relates generally to the field of molecular biology, cancer biology and rheumatology. More particularly, it concerns connexin (Cx)43 hemichannel-binding antibodies and their use for the treatment and detection of disease, such as cancer, neurological injury and osteoarthritis.

2. Description of Related Art

Traumatic spinal injury (SCI) and traumatic brain injury (TBI) are serious health problems worldwide and over 1.5 million patients annually are diagnosed with traumatic brain and spinal cord injuries. Patients with SCI and TBI not only can lose neuronal function, but are at greater risk for neuropathic pain and other complications associated with loss of nervous control. Secondary injury accounts for major post-traumatic loss of neurological function. Part of the post-injury neuroinflammatory process is the activation of astrocytes and formation of a glial scar resulting in an impermeable milieu for axonal regeneration. The therapeutic goals include limitation of the size of lesions and axonal loss with the innovative approach of targeting astrocytes, a class of support cells that play a major role in supporting neuronal function and glial scar formation. However, there remains a need for compositions that can be used to successfully limit glial scar formation.

Bone tissues are a preferred site of breast and prostate cancer metastasis. Bone metastasis occurs in up to 75% of patients with advanced cancers. Currently, there is no cure for metastatic breast cancer and no reliable intervention drug for treating bone metastasis that has minimal side effects.

Osteoarthritis (OA) is a prevalent disease that affects approximately 20% of U.S. adults. This disease causes the degeneration of joints including articular cartilage and subchondral bone. The pathology of OA is characterized by a loss of articular cartilage leading to narrowing of joint space, increased joint friction and potential structure remodeling. Current treatment includes exercise, lifestyle change and analgesics. If symptom becomes severe, joint replacement surgery is normally performed. Thus far, there is no specific pharmaceutical intervention available for the treatment of OA.

Connexin hemichannels play important roles in the cell and tissue function, and abnormal function of connexin hemichannels may be involved various pathological conditions, such as those described above. Thus, there remains a need for additional therapies for treating pathological conditions associated with hemichannels activity (e.g., inflammation, SCI, TBI, bone metastasis), as well as methods for identifying such therapies.

SUMMARY OF THE INVENTION

In a first embodiment, the invention provides a method of treating or preventing cancer or bone metastasis in a subject having a cancer comprising administering to the subject an effective amount of an antibody that binds to a connexin 43 (Cx43) hemichannel and enhances channel opening or an expression vector encoding the antibody (such as the Ab2 antibodies detailed herein). In a further embodiment, there is provided a method of treating or preventing osteoporosis or osteopenia in a subject comprising administering to the subject an effective amount of an antibody that binds to a connexin 43 (Cx43) hemichannel and enhances channel opening or an expression vector encoding the antibody (such as the Ab2 antibodies detailed herein). In certain aspects, the method comprises administering an effective amount of the antibody to the subject. In further aspects, the method comprises administering an effective amount of an expression vector encoding the antibody to the subject. In some aspects, the cancer is breast cancer, prostate cancer (e.g., with bone metastasis), or osteosarcoma. In further aspects, the cancer is a cancer having bone metastases.

In further aspects, the expression vector encoding the antibody may be administered in a pharmaceutically acceptable composition. In certain aspects, the antibody may be administered systemically. In other aspects, the antibody may be administered intravenously, intradermally, intratumorally, intramuscularly, intraperitoneally, subcutaneously, or locally.

In several aspects, the antibody may comprise a first $V_H$ CDR identical to SEQ ID NO: 19, a second $V_H$ CDR identical to SEQ ID NO: 20, a third $V_H$ CDR identical to SEQ ID NO: 21, a first $V_L$ CDR identical to SEQ ID NO: 49, a second $V_L$ CDR identical to SEQ ID NO: 50, and a third VL CDR identical to SEQ ID NO: 51. In some aspects, the antibody is a humanized antibody. In certain aspects, the antibody may comprise a VH amino acid sequence at least 90% identical to SEQ ID NO: 58 and/or a VL amino acid sequence at least 90% identical to SEQ ID NO: 63. In a further aspect, the antibody comprises a VH amino acid sequence according to SEQ ID NO: 58 and/or a VL amino acid sequence according to SEQ ID NO: 63.

In still further aspects, the method may additionally comprise administering at least a second anticancer therapy to the subject. In certain aspects, the second anticancer therapy is a surgical therapy, chemotherapy, radiation therapy, cryotherapy, hormonal therapy, immunotherapy or cytokine therapy.

In a further embodiment, the invention provides a method of treating or preventing neurodegenerative disease or a neurological injury in a subject comprising administering to the subject an effective amount of an antibody that binds to a connexin 43 (Cx43) hemichannel and inhibits channel opening or an expression vector encoding the antibody (such as the Ab1 antibodies detailed herein). In several aspects, the method comprises administering an effective amount of the antibody to the subject. In other aspects, the method may comprise administering an effective amount of an expression vector encoding the antibody to the subject.

In some aspects, the method may additionally be defined as a method for treating or preventing a neurodegenerative disease. In a further aspect, the neurodegenerative disease may be multiple sclerosis or Alzheimer's disease. In other aspects, the method may additionally be defined as a method for treating or preventing a neurological injury. In certain aspects, the neurological injury comprises a spinal cord injury (SCI), stroke or traumatic brain injury (TBI). In some specific aspects, the subject has or has been diagnosed with a neurological injury. In several aspects, the expression vector encoding the antibody is administered in a pharmaceutically acceptable composition. In certain aspects, the antibody may be administered systemically. In further aspects, the antibody is administered intravenously, intradermally, intramuscularly, intraperitoneally, subcutaneously, or locally.

In several aspects, the antibody comprises a first $V_H$ CDR identical to SEQ ID NO: 19, a second $V_H$ CDR identical to SEQ ID NO: 20, a third $V_H$ CDR identical to SEQ ID NO: 21, a first $V_L$ CDR identical to SEQ ID NO: 31, a second $V_L$ CDR identical to SEQ ID NO: 32, and a third $V_L$ CDR identical to SEQ ID NO: 33. In some aspects, the antibody is a humanized antibody. In certain aspects, the antibody comprises a VH amino acid sequence at least 90% identical to SEQ ID NO: 58 and/or a VL amino acid sequence at least 90% identical to SEQ ID NO: 60. In some particular aspects, the antibody comprises a VH amino acid sequence according to SEQ ID NO: 58 and/or a VL amino acid sequence according to SEQ ID NO: 60.

In yet a further embodiment, there is provided a recombinant connexin 43 (Cx43) hemichannel-binding antibody. In certain aspects, the antibody comprises a first $V_H$ CDR identical to SEQ ID NO: 19, a second $V_H$ CDR identical to SEQ ID NO: 20, a third $V_H$ CDR identical to SEQ ID NO: 21, a first $V_L$ CDR identical to SEQ ID NO: 49, a second $V_L$ CDR identical to SEQ ID NO: 50, and a third $V_L$ CDR identical to SEQ ID NO: 51. In some aspects, the antibody is a humanized antibody. In certain particular aspects, the antibody comprises a VH amino acid sequence at least 90% identical to SEQ ID NO: 58 and/or a VL amino acid sequence at least 90% identical to SEQ ID NO: 63. In a specific aspect, the antibody may comprise a VH amino acid sequence according to SEQ ID NO: 58 and/or a VL amino acid sequence according to SEQ ID NO: 63.

In several aspects, the antibody may comprise a first $V_H$ CDR identical to SEQ ID NO: 19, a second $V_H$ CDR identical to SEQ ID NO: 20, a third $V_H$ CDR identical to SEQ ID NO: 21, a first $V_L$ CDR identical to SEQ ID NO: 31, a second $V_L$ CDR identical to SEQ ID NO: 32, and a third $V_L$ CDR identical to SEQ ID NO: 33. In certain aspects, the antibody is a humanized antibody. In some aspects, the antibody comprises a VH amino acid sequence at least 90% identical to SEQ ID NO: 58 and/or a VL amino acid sequence at least 90% identical to SEQ ID NO: 60. In certain specific aspects, the antibody comprises a VH amino acid sequence according to SEQ ID NO: 58 and/or a VL amino acid sequence according to SEQ ID NO: 60.

In still yet a further embodiment, the invention provides a method of treating cancer in a subject comprising administering an effective amount of a pharmaceutical composition comprising an antibody according to the embodiments and aspects described above or an expression vector encoding an antibody according to the embodiments and aspects described above to the subject. In some aspects, the pharmaceutical composition comprises an expression vector encoding an antibody according to the embodiments and aspects described above to the subject. In other aspects, the pharmaceutical composition comprises an antibody according to the embodiments and aspects described above to the subject. In several aspects, the method may further be defined as a method for inhibiting or preventing cancer bone metastasis in the subject. In certain aspects, the pharmaceutical composition may be administered systemically. In specific aspects, the pharmaceutical composition is administered intravenously, intradermally, intratumorally, intramuscularly, intraperitoneally, subcutaneously, or locally.

In some aspects, the pharmaceutical composition may comprise a first $V_H$ CDR identical to SEQ ID NO:19, a second $V_H$ CDR identical to SEQ ID NO:20, a third $V_H$ CDR identical to SEQ ID NO:21, a first $V_L$ CDR identical to SEQ ID NO:31, a second $V_L$ CDR identical to SEQ ID NO:32, and a third $V_L$ CDR identical to SEQ ID NO:33. In several aspects, the method may further comprise administering at least a second anticancer therapy to the subject. In further aspects, the second anticancer therapy is a surgical therapy, chemotherapy, radiation therapy, cryotherapy, hormonal therapy, immunotherapy or cytokine therapy.

In a further aspect, the invention provides a method of treating an inflammatory disease, a neurodegenerative disease or a neurological injury in a subject comprising administering an effective amount of a pharmaceutical composition comprising an antibody according to the embodiments and aspects described above or an expression vector encoding an antibody according to the embodiments and aspects described above to the subject (an antibody that binds to a Cx43 hemichannel and inhibits channel opening, such as the Ab1 antibodies detailed herein). In certain aspects, the pharmaceutical composition comprises an expression vector encoding an antibody according to the embodiments and aspects described above to the subject. In specific aspects, the pharmaceutical composition comprises an antibody according to the embodiments and aspects described above to the subject.

In further aspects, the method may additionally be defined as a method for treating or preventing an inflammatory disease comprising administering to the subject an effective amount of an antibody that binds to a Cx43 hemichannel and inhibits channel opening or an expression vector encoding the antibody (such as the Ab1 antibodies detailed herein). In some specific aspects, the inflammatory disease is osteoarthritis. In some aspects, a method is provided for promoting wound healing, such as skin or cornea wound healing comprising administering to a subject an effective amount of an antibody that binds to a connexin 43 (Cx43) hemichannel and inhibits channel opening or an expression vector encoding the antibody (such as the Ab1 antibodies detailed herein). In other aspects, the method may additionally be defined as a method for treating or preventing a neurodegenerative disease. In certain particular aspects, the neurodegenerative disease is multiple sclerosis or Alzheimer's. In several aspects, the method may further be defined as a method for treating or preventing a neurological injury. In some particular aspects, the neurological injury comprises a spinal cord injury (SCI), traumatic brain injury (TBI), or stroke. In certain aspects, the subject has or has been diagnosed with a neurological injury.

In some aspects, the pharmaceutical composition may be administered systemically. In specific aspects, the pharmaceutical composition is administered intravenously, intradermally, intratumorally, intramuscularly, intraperitoneally, subcutaneously, or locally.

In certain embodiments there are also provided antibodies directed against hemichannel polypeptides, and nucleic acid molecules encoding such antibodies. In certain aspects an antibody of the embodiments binds an epitope having an amino acid sequence of FLSRPTEKTI (SEQ ID NO: 13), KRDPCPHQVD (SEQ ID NO: 14), or LSAVYTCKR (SEQ ID NO: 15). In a particular aspect an antibody binds an epitope having an amino acid sequence of FLSRPTEKTI (SEQ ID NO: 13).

In further embodiments the antibodies for use according to the embodiments can be any of those described in international (PCT) patent publication no. WO 2015, 027120, which is incorporated herein by reference. In one embodiment, the invention provides an isolated antibody which specifically binds to hemichannels, comprising a heavy chain having an amino acid sequence of SEQ ID NO:2 and a light chain having an amino acid sequence of SEQ ID NO:4.

In certain aspects a first heavy chain region comprises an amino acid sequence having an amino acid sequence of residues 13 to 37 of SEQ ID NO:2; a second heavy chain region having an amino acid sequence corresponding to residues 46 to 66 of SEQ ID NO:2; and a third heavy chain region comprising an amino acid sequence having an amino acid sequence of residues 97 to 116 of SEQ ID NO:2.

In another aspect a first light chain region comprises an amino acid sequence having an amino acid sequence of residues 9 to 40 of SEQ ID NO:4; a second light chain region having an amino acid sequence corresponding to residues 49 to 58 of SEQ ID NO:4; and a third light chain region comprising an amino acid sequence having an amino acid sequence of residues 64 to 108 of SEQ ID NO:4.

In one embodiment, the invention provides an isolated antibody which specifically binds to hemichannels and gap junctions, comprising a heavy chain having an amino acid sequence of SEQ ID NO:6 and a light chain having an amino acid sequence of SEQ ID NO:8.

In certain aspects a first heavy chain region comprises an amino acid sequence having an amino acid sequence of residues 13 to 37 of SEQ ID NO: 6; a second heavy chain region having an amino acid sequence corresponding to residues 46 to 66 of SEQ ID NO:6; and a third heavy chain region comprising an amino acid sequence having an amino acid sequence of residues 97 to 116 of SEQ ID NO:6.

In another aspect a first light chain region comprises an amino acid sequence having an amino acid sequence of residues 9 to 42 of SEQ ID NO: 8; a second light chain region having an amino acid sequence corresponding to residues 51 to 60 of SEQ ID NO: 8; and a third light chain region comprising an amino acid sequence having an amino acid sequence of residues 66 to 125 of SEQ ID NO:8.

In one embodiment, the invention provides an isolated antibody which specifically binds to gap junctions, comprising a heavy chain having an amino acid sequence of SEQ ID NO:10 and a light chain having an amino acid sequence of SEQ ID NO:12.

In certain aspects a first heavy chain region comprises an amino acid sequence having an amino acid sequence of residues 10 to 34 of SEQ ID NO: 10; a second heavy chain region having an amino acid sequence corresponding to residues 43 to 59 of SEQ ID NO:10; and a third heavy chain region comprising an amino acid sequence having an amino acid sequence of residues 94 to 109 of SEQ ID NO:10.

In another aspect a first light chain region comprises an amino acid sequence having an amino acid sequence of residues 9 to 40 of SEQ ID NO:12; a second light chain region having an amino acid sequence corresponding to residues 49 to 58 of SEQ ID NO:12; and a third light chain region comprising an amino acid sequence having an amino acid sequence of residues 64 to 108 of SEQ ID NO:12.

In certain aspects antibodies include full length antibodies, antibody fragments, single chain antibodies, bispecific antibodies, minibodies, domain antibodies, synthetic antibodies and antibody fusions, and fragments thereof A further embodiment provides a pharmaceutical composition comprising an antibody as described herein with a pharmaceutically acceptable carrier. Also provided is an antibody or a pharmaceutical composition of the invention for use as a medicament or for use in therapy for cancer and to inhibit cancer metastasis.

A further embodiment provides a method of treating or preventing cancer metastasis. A method of treating can comprise administering to a subject in need thereof an effective amount of an isolated antibody described herein. Also provided is the use of an antibody as described herein in the manufacture of a medicament for the treatment or prevention of cancer metastasis.

Certain aspects are directed to in vitro methods of using an antibody, compounds or reagents to suppress inflamatory reactions in chondrocytes. In certain aspects methods are directed to determining the effect on inhibition of Cx43 hemichannel opening in chondrocytes by (i) determining hemichannel opening by dye uptake assay, using Lucifer yellow or Alexa dyes, (ii) assessing inhibitory effects on hemichannels opening by IL-1β, (iii) test inhibitory effects of the reagents on hemichannels opening by mechanical loading in the form of fluid flow shear stress.

Certain aspects are directed to methods of determining the effect of an antibody, compounds or reagents on suppressing of inflammatory responses evoked by IL-1β and mechanical loading by (i) determining the inhibition of activation of nuclear factor-kappaB (NF-κB) induced by IL-1β, (ii) determining the inhibition of activation of NF-κB induced by fluid flow shear stress.

Other aspects are directed to an in vivo method of using a monoclonal antibody, compounds or reagents to treat OA or identify the same comprising (i) injecting antibody, compound or reagent into knee cap cavity, (ii) assessing the inhibition of activation of NF-κB induced by IL-1β, (iii) assessing OA development by X-ray, histological analysis and physical movement.

As used herein, the term "antigen" is a molecule capable of being bound by an antibody or T-cell receptor. In certain embodiments, binding moieties other than antibodies and be engineered to specifically bind to an antigen, e.g., aptamers, avimers, and the like.

The term "antibody" or "immunoglobulin" is used to include intact antibodies and binding fragments/segments thereof. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Typically, fragments compete with the intact antibody from which they were derived for specific binding to an antigen. Fragments include separate heavy chains, light chains, Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin Exp Immunol* 79:315-21, 1990; Kostelny et al., *J. Immunol.* 148:1547-53, 1992.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

The term "providing" is used according to its ordinary meaning "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

HMAb1 that were subjected to immunohistochemistry for the astrocyte marker GFAP. The lesion boundary is indicated with a dotted white line. (G) GFAP immunolabeling was quantified as the mean intensity multiplied by area of positive stain. Results are expressed as a percentage of Sham surgery, IgG treated mice. Results are average with SEM. *p<0.05, ***p<0.001 compared to Igg w/Tukey's HSD n=3-4.

Figures 4A, 4B, 4C:
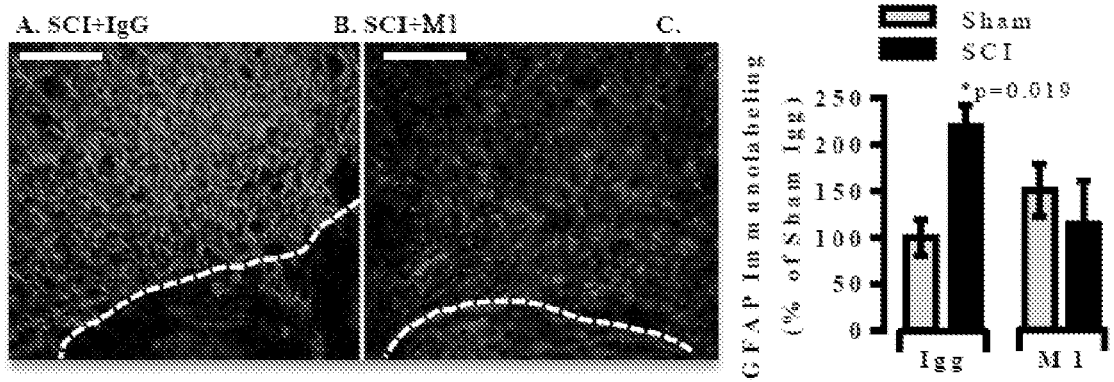

FIGS. 4A-4C—Mice were subjected to SCI and treated with IgG or anti-Cx43 antibody (M1) at 30 minutes post injury. Two weeks after injury, tissue sections were analyzed for expression of the astrocyte marker GFAP. Representative images of spinal cord in (A) IgG treated or (B) M1-treated mice. The white dotted line marks the area of lesion. C) Quantification of images from n=3-5 mice shows averages with SEM of GFAP immunolabeling in sections. * significance tested using 2-way ANOVA then Tukey's HSD.

Figures 5A, 5B:
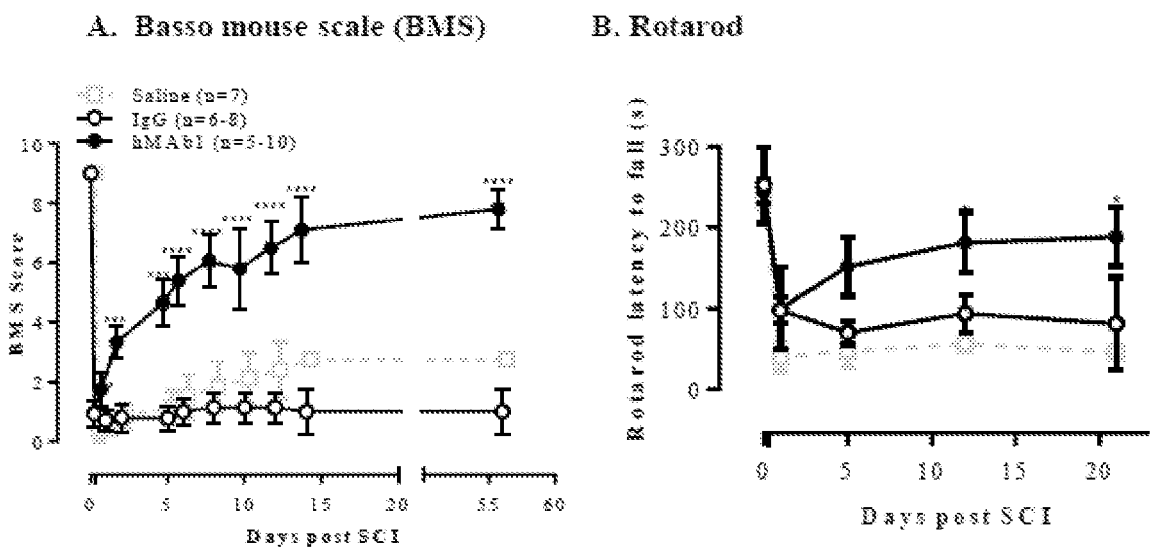

FIGS. 5A-5B—HMAb1 treatment improved the recovery of physical activity and coordination after SCI. Mice were subjected to a single SCI and treated 30 minutes after injury with IP saline, control IgG, or human-mouse chimeric anti-Cx43 antibody (HMAb1) (25 mg/kg). Behavioral measurements are in mice with a BMS score of 0-3 at the 6 hour time point after injury. (A) BMS: Hind limb function; 0=no hind limb function and 9=completely normal hind limb function. (B) Rotarod: Mice were tested for the ability to remain on an accelerating rotarod for up to 300 seconds to measure motor coordination. Results are averages with SEM. *p<0.05, p<0.01, *p<0.001 compared to Igg w/Tukey's HSD.

FIGS. 6A-6G—Mice were subjected to a single SCI and treated 30 minutes after injury with IP saline, control Igg, or HMAb1 (25 mg/kg). Neuronal dendrites were measured by immunolabeling against the neuronal marker MAP2. (A-F) Representative images of spinal cords in mice treated with (A-C) control IgG or (D-F) HMAb1 that were subjected to immunohistochemistry. The lesion boundary is indicated with a dotted white line. (G) MAP2 immunolabeling was quantified as the mean intensity multiplied by area of positive stain. Results are expressed as a percentage of Sham surgery, IgG treated mice. Results are averages with SEM. *p<0.05, "p<0.001 with Tukey's HSD, n=3-4.

FIG. 7A-7G—Mice were subjected to a single SCI and treated 30 minutes after injury with IP saline, control Igg, or HMAb1 (25 mg/kg). Neuronal nuclei were measured by immunolabeling against the neuronal marker NeuN. (A-F) Representative images of spinal cords in mice treated with (A-C) control IgG or (D-F) HMAb1 that were subjected to immunohistochemistry. The lesion boundary is indicated with a dotted white line. (G) NeuN immunolabeling was quantified as the mean intensity multiplied by area of positive stain. Results are expressed as a percentage of Sham surgery, IgG treated mice.

Figures 8A, 8B, 8C:
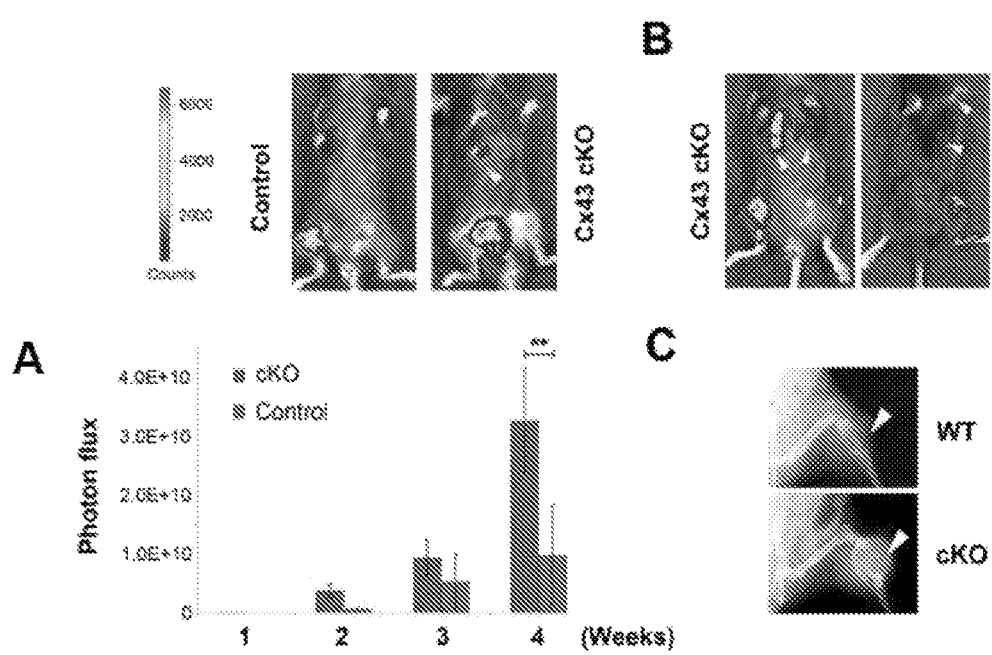

FIGS. 8A-8C—Breast cancer growth in bone was suppressed by human-mouse chimeric anti-Cx43 antibody HMAb2 (this antibody comprises the same murine variable domains and CDRs as the "M2" antibody). Py8119-Luc cells were injected into right tibias of control and cKO female mice. The left tibias were injected with PBS as controls. (A) The tumor growth was recorded every week for 4 weeks by bioluminescence imaging and quantified. Data are presented as means±SEM. **, P<0.01. n=7 per group. (B) Representative images of Cx43 cKO mice with tumor spread to the lungs and to the brain shown with white arrowheads. (C) Representative X-ray radiographs with tibia injected with Py8119 cells indicate where the tumor cells were injected and osteolytic lesions occurred (arrowheads). The left tibias injected with PBS showed no osteolytic lesions.

Figure 9A:
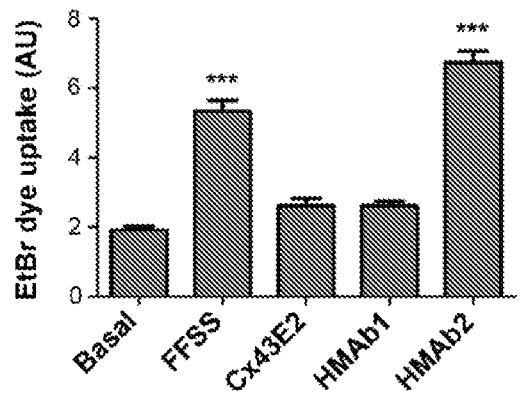
Figure 9B:
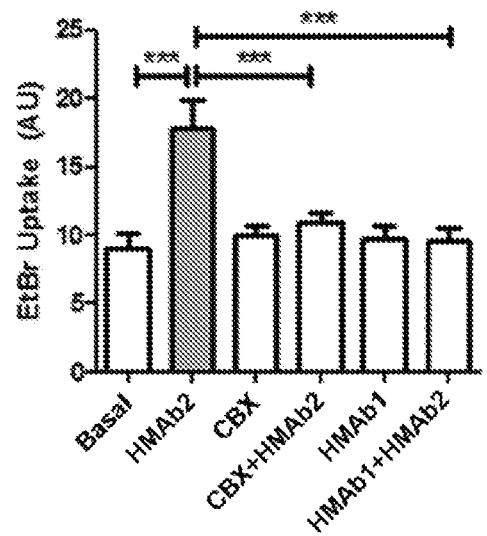

FIGS. 9A-9B—Cx43 hemichannels in MLO-Y4 osteocytes (A) or primary mouse osteocytes (B) were activated by HMAb2, but blocked by HMAb1. The cells were incubated with E2 (polyclonal), HMAb1 and HMAb2 antibody or carbenoxolone (CBX), a connexin channel blocker. Ethium bromide (EtBr) dye uptake assay was performed. Data presented as SEM. Compared to basal control, ***, P<0.001.

Figures 10A, 10B:
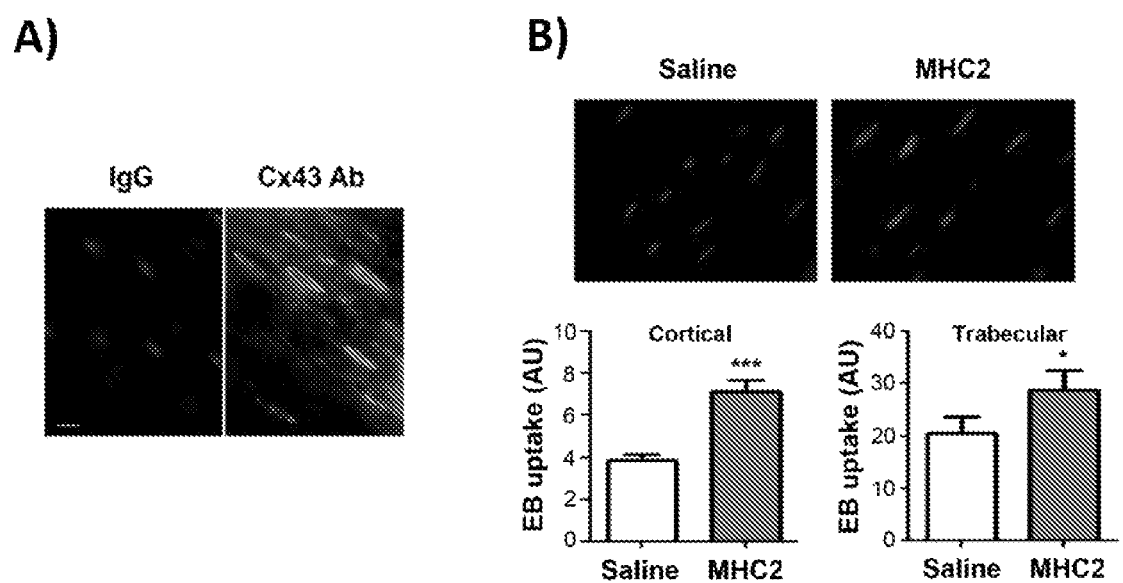

FIGS. 10A-10B—Activation of Hemichannels by MHAb2 in Osteocytes in vivo. Evans blue dye was injected into tail vein of WT mice and 25 μg/ml MHAb2 was IP injected. Mice were sacrificed two hours after injection and perfused with PBS. Tibias were isolated and fixed tibial bone tissue sections were prepared. (A) Presence of antibodies was detected with rhodamine-conjugated anti-human IgG. Bar, 50 μm. (B) Dye uptake was measured in cortical and trabecular bones by Evans blue (EB) fluorescence and quantified. *, P<0.05; ***, P<0.001.

Figure 11A:
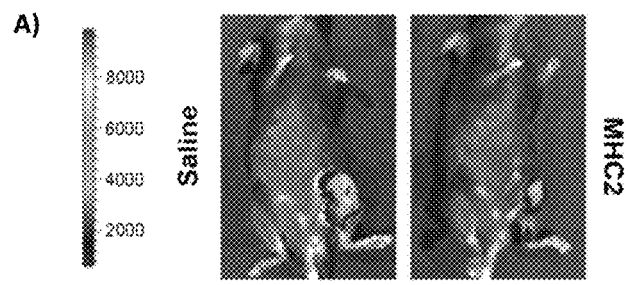
Figure 11C:
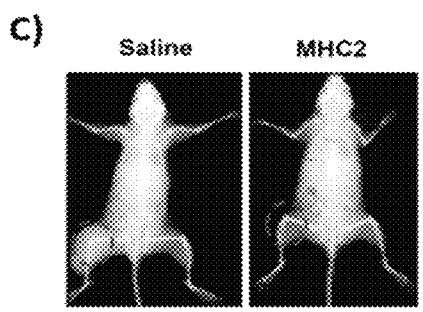
Figure 11B:
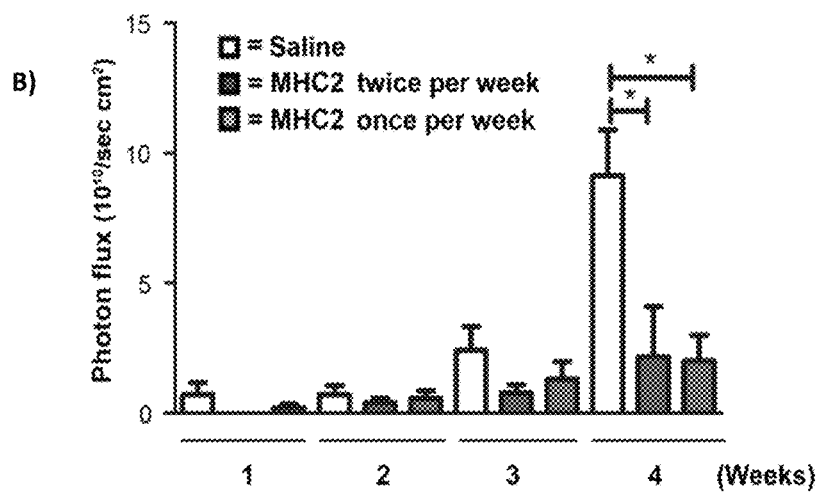

FIGS. 11A-11C—HMAb2 suppresses osteolytic growth of breast cancer cells and protects bone from fractures. (A) Py8119-Luc breast cancer cells were injected into tibias of female mice. (B) HMAb2 at 25 mg/kg was i.p. injected either once or twice per week for four weeks. Saline was injected twice per week in control mice. The tumor growth was recorded every week for 4 weeks by bioluminescence imaging and quantified (lower panel). Data are presented as means±SEM. n=6 for HMAb2 and saline. (C) The MHAb2 or saline injected mice were imaged by X-ray. *, P<0.05.

Figure 12:
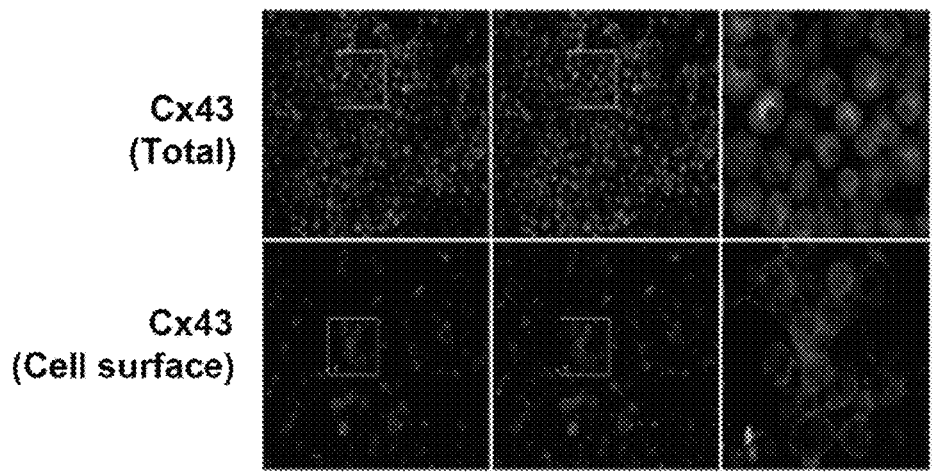

FIG. 12—Cx43 is abundantly expressed in chondrocytes. Primary chondrocytes isolated from mouse bone were immunostained with anti-Cx43 antibody against C-terminal domain (Total) in permeable cells and Cx43E2 antibody in non-permeable cells.

Figure 13:
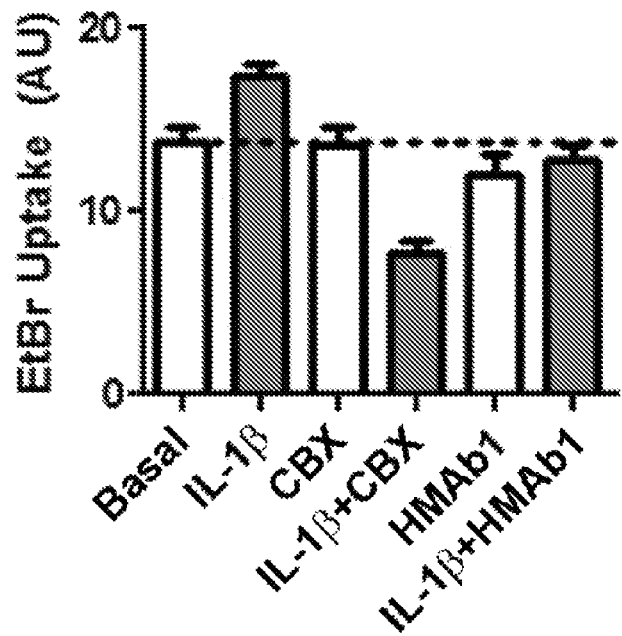

FIG. 13—HMAb1 blocked Cx43 hemichannels in chondrocytes. Primary chondrocytes isolated from mouse bone were pre-treated with carbenoxolone (connexin channel blocker) or HMAb1 antibody and then treated with or without IL-1β. Ethidium bromide dye uptake assay was performed to determine hemichannel activity.

Figure 14:
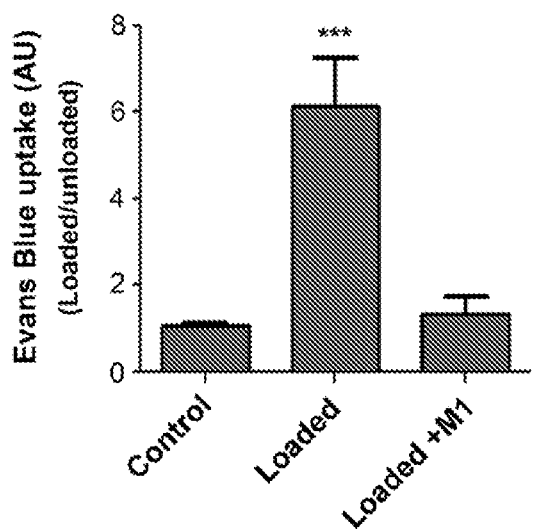

FIG. 14—HMAb1 blocked hemichannel activity in mouse chondrocytes in vivo. Evans blue dye was injected into tail vein of WT mice. Cx43(M1) mAb (25 mg/kg) was i.p. injected 2 hrs before dye injection. 30 min after dye injection, left tibias were mechanically loaded once for 10 min. Dye uptake was measured by Evans blue (EB) fluorescence and quantified. P<0.001. n=3.

Figure 15:
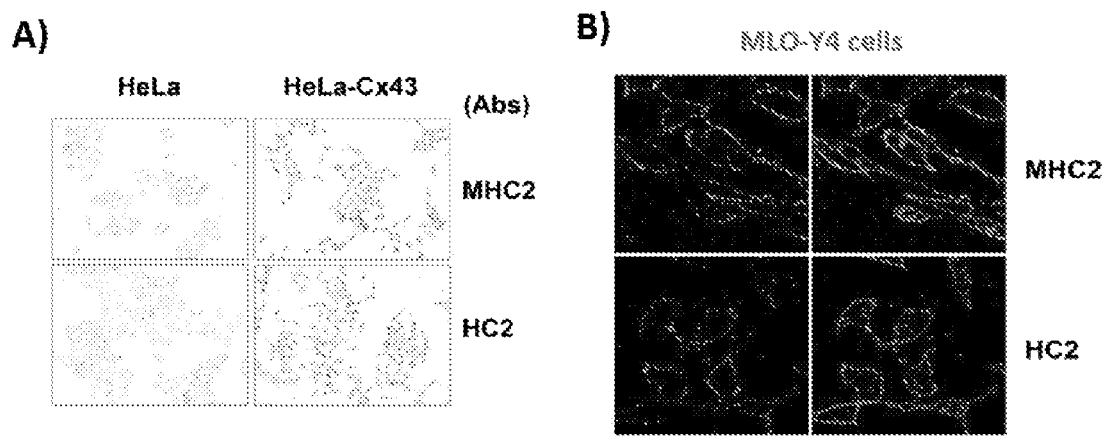

FIG. 15—Both HMAb2 and HAb2 antibodies recognize Cx43 and bind Cx43 on osteocyte cell surface. (A) Parental HeLa or HeLa cells expressing Cx43 were immunolabeled with HMAb2 (MHC2) or HAb2 (HC2) antibody. (B) Non-permeable osteocyte MLO-Y4 cells were immunofluoresently labeled with anti-HMAb2 (MHC2) or HAb2 (HC2) antibody.

Figure 16:
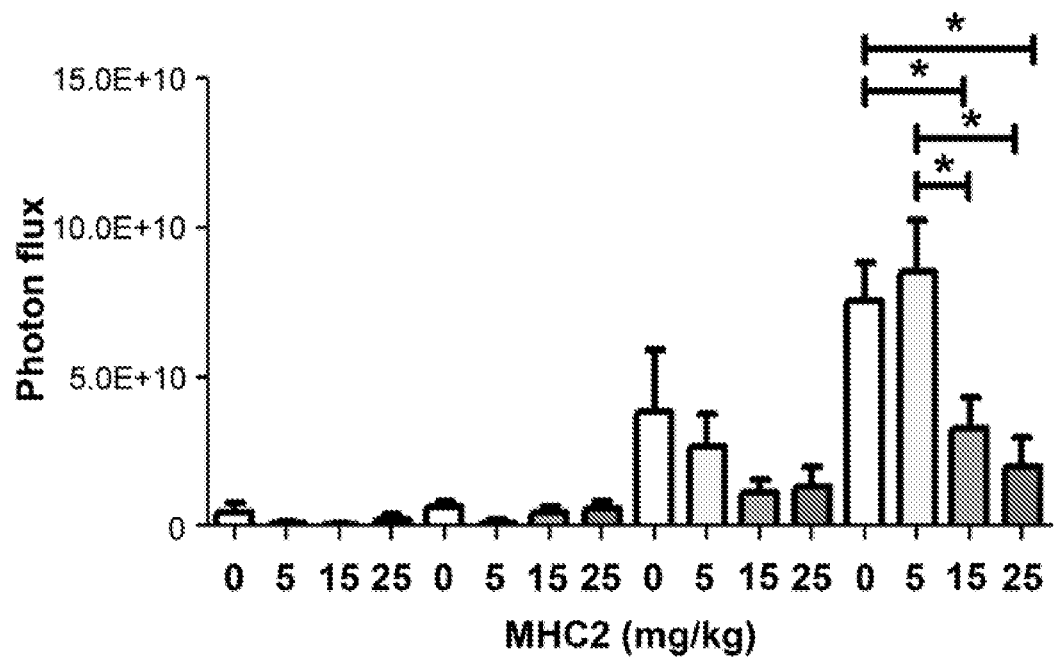

FIG. 16—Dose-dependent inhibition of osteolytic breast cancer growth by MHAb2. Py8119-Luc breast cancer cells were injected into tibias of female mice. HMAb2 at 5, 15 and 25 mg/kg was i.p. injected once per week for four weeks. Saline was injected once per week in control mice. The tumor growth was recorded every week for 4 weeks by bioluminescence imaging and quantified. Data are presented as means±SEM. n=6 for HMAb2 and saline. *, P<0.05.

FIGS. 17A-17D—HMAb2 increases trabecular bone mass, volume and thickness. 4 month-old mice were i.p. injected with 25 mg/kg HMAb2 antibody or saline once a week for two weeks. The bone parameters, (A) bone volume; (B) Trabecular thickness; (C) trabecular number; and (D) bone mineral density (BMD) were determined by mciroCT imaging and quantified. Data are presented as means±SEM. n=6; *, P<0.05; **, P<0.01.

FIGS. 18A-18B—Inhibition of osteolytic human breast cancer growth by MHAb2. (A) MDA-MB231 human breast cancer cells were injected into tibias of female immune-compromised nude mice. HMAb2 at 25 mg/kg was i.p. injected once per week for 7 weeks. Saline or human IgG was injected once per week in control mice. The tumor growth was recorded every week for 7 weeks by bioluminescence imaging and quantified. Data are presented as means±SEM. n=6. *, P<0.05. (B) Mice were sacrificed after 7 weeks and tumors were isolated.

Figure 19:
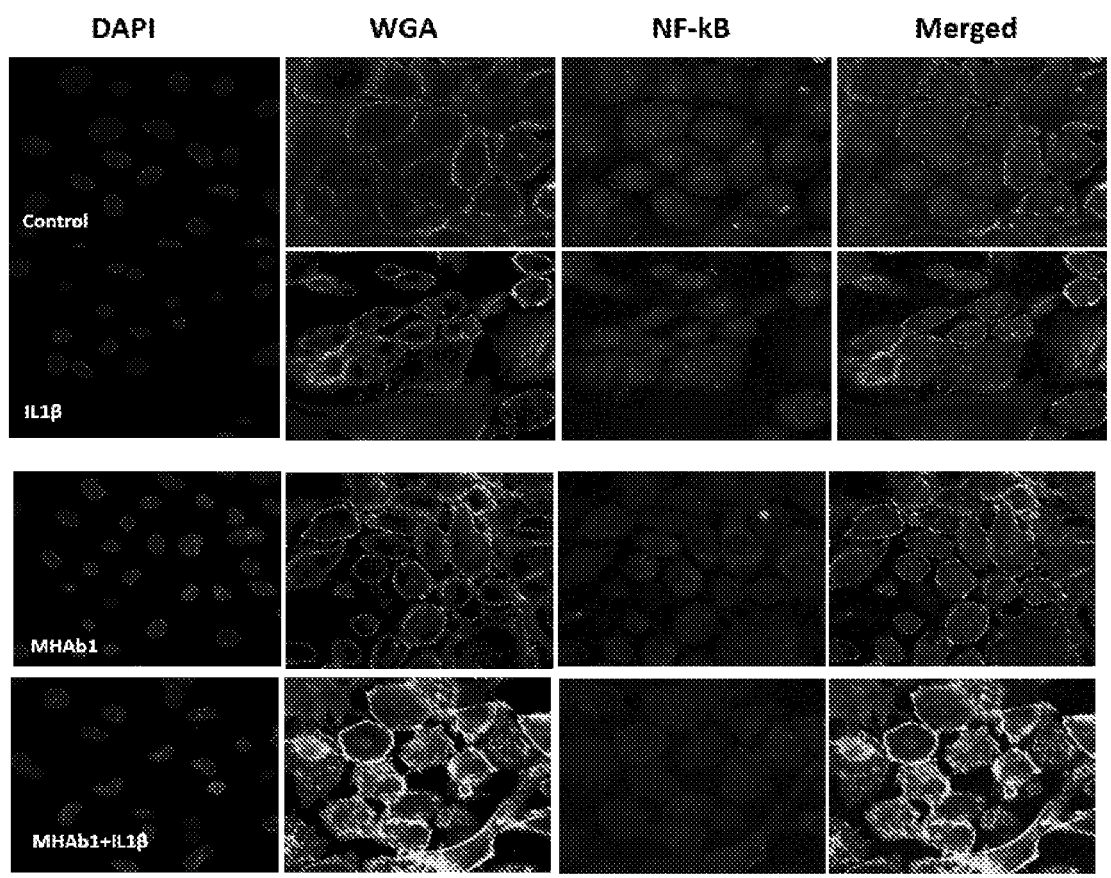

FIG. 19—MHAb1 suppresses inflammatory response by inhibiting nuclear translocation of NF-kB. Primary mouse chondrocytes were treated with or without interleukin (IL) 10 and MHAb1, fixed and immunolabeled with antibody NF-kB antibody and countered labeled with FITC-WGA. The merged images are shown in right panels.

DESCRIPTION

Various cells are able to communicate with each other and with the extracellular environment through hemichannels and gap junctions formed by the protein connexin. Connexin proteins are ubiquitously expressed throughout the body. Six connexin proteins make up one hemichannel, and 2 hemichannels make up 1 gap junction channel Gap junctions are a cluster of channels that are located in the plasma membrane between adjoining cells and they mediate intercellular communication. Hemichannels are a separate entity from gap junction channels. Hemichannels permit the exchange of molecules between the intracellular compartments and the extracellular environment.

Osteocytes express hemichannels known as connexin (Cx) 43 hemichannels. These osteocyte hemichannels are normally closed and can be opened when exposed to mechano-stimulation, which leads to the release of various factors into the bone microenvironment. The factors released by hemichannel opening can mediate other processes that can decrease tumor cell migration and bone metastasis.

Certain embodiments are directed to methods of identifying reagents that modulate the opening of connexin hemichannels. In certain aspects, the methods identify compounds or drugs that positively modulate the opening of connexin hemichannels. Other embodiments are directed to methods of treating cancer by administering a compound that open hemichannels to a patient having cancer, such as breast cancer or prostate cancer. In certain aspects, the patient has a primary tumor. In certain aspects, compounds that open Cx43 hemichannels can be used to inhibit or reduce metastasis to the bone. In other aspects, compounds that open Cx43 channels are used to treat osteoporosis, osteopenia, or osteosarcoma.

Cancer metastasis occurs when a cancer spreads from the part of the body where it originated (e.g., breast or prostate) to other parts of the body (e.g., liver or bone) and establishes a secondary tumor. The bone is one of the most common sites of cancer metastasis. Cancers that metastasize to bone include, but are not limited to breast cancer, prostate cancer, lung cancer, and skin cancers (e.g., melanoma). Bone metastasis can be identified in up to 75% of patients with advanced breast and prostate cancers. Bone metastasis (mets) are associated with many significant clinical and quality of life consequences, such as, but not limited to intractable pain, pathological fractures, spinal cord and nerve compression, bone marrow infiltration, and impaired motility. In many cases the systemic presence of a cancer can also make the cancer incurable.

Normal bone is made up of three major cell types: bone-forming osteoblasts, bone-resorbing osteoclasts, and osteocytes. Osteocytes make up approximately 95% of bone cells and maintain the bone remodeling process by coordinating osteolytic and osteoblastic activities. When cancer cells invade the bone, many of the normal bone functions are affected. Cancer cells interact with the local microenvironment to promote cancer cell survival via bone destruction and vascularization.

Cx43 hemichannels in osteocytes have been shown to open by treatment with alendronate (AD), an efficacious and commonly used bisphosphonate drug. Bisphosphonates are a class of drugs known for treating many bone disorders including bone metastasis. Powles et al. have shown administration of bisphosphonates to be associated with a decrease in the incidence of bone metastasis and a decrease in death rate in patients with breast cancer. AD has been associated with decreased tumor growth as well as reduced bone destruction and pain. AD inhibits osteoclast activity and induces the opening of Cx43 hemichannels in osteocytes (Plotkin et al., 2002). However, AD administration is accompanied by multiple, severe side-effects.

I. ANTIBODIES

Certain aspects of the invention are directed to antibodies that modulate, positively or negatively, the function of hemichannels. An example of identifying and isolating a monoclonal antibody is described below.

The term "CDR" as used herein refers to a Complementarity Determining Region of an antibody variable domain. Systematic identification of residues included in the CDRs have been developed by Kabat et al. (1991, Sequences of Proteins of Immunological Interest, 5th Ed., United States Public Health Service, National Institutes of Health, Bethesda). Variable light chain (VL) CDRs are herein defined to include residues at positions 27-32 (CDR1), 50-56 (CDR2), and 91-97 (CDR3). Variable heavy chain (VH) CDRs are herein defined to include residues at positions 27-33 (CDR1), 52-56 (CDR2), and 95-102 (CDR3).

As will be appreciated by those in the art, the CDRs disclosed herein may also include variants. Generally, the amino acid identity between individual variant CDRs is at least 90%, 91%, 92%, 93%, 94%, 95%, 96%, 97%, 98%, 99%, or 100%. Thus, a "variant CDR" is one with the specified identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities as described herein.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

The term "antigen-binding portion" of an antibody (or simply "antibody portion"), as used herein, refers to one or more fragments of an antibody that retain the ability to specifically bind to an antigen (e.g., hemichannel). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL/VK, VH, CL and CH1 domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3rd ed. 1993); (iv) a Fd fragment consisting of the VH and CH1 domains; (v) a Fv fragment consisting of the VL and VH domains of a single arm of an antibody; (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Suitably there is no significant cross-reaction or cross-binding with undesired substances. The affinity of the antibody will, for example, be at least about 5-fold, such as 10-fold, such as 25-fold, especially 50-fold, and particularly 100-fold or more, greater for a target molecule than its affinity for a non-target molecule. In some embodiments, specific binding between an antibody or other binding agent and an antige means a binding affinity of at least $10^6$ M-$^1$. Antibodies may, for example, bind with affinities of at least about $10^7$ M-$^1$, such as between about $10^8$ M-$^1$ to about $10^9$ M-$^1$, about $10^9$ M-$^1$ to about $10^{10}$ or about 10-$^{10}$ M-$^1$ to about $10^{11}$ M-$^1$. Antibodies may, for example, bind with an EC50 of 50 nM or less, 10 nM or less, 1 nM or less, 100 pM or less, or more preferably 10 pM or less.

In certain embodiments, an antibody or a fragment thereof that binds to at least a portion of Cx43 protein and inhibits Cx43 signaling and cancer cell proliferation are contemplated. Preferably, the anti-Cx43 antibody is a monoclonal antibody or a humanized antibody. Thus, by known means and as described herein, polyclonal or monoclonal antibodies, antibody fragments, and binding domains and CDRs (including engineered forms of any of the foregoing) may be created that are specific to Cx43 protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the VII and Cm domains; (iii) the "Fv" fragment consisting of the $V_L$ and $V_H$ domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VII domain and a VL domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a Cx43 extracellular domain protein, in order to produce antibodies specific for Cx43 protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a Cx43 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells may be isolated from freshly prepared rabbit peripheral blood mononuclear cells of immunized rabbits and further selected for Cx43 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. Cx43 specific binding Fab may be selected out through multiple rounds enrichment panning and sequenced. Selected Cx43 binding hits may be expressed as full length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, bguinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to Cx43 will have the ability to neutralize or counteract the effects of Cx43 regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds Cx43.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against Cx43, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radio-labels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluene sulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. TREATMENT OF DISEASES

Certain aspects of the present embodiments can be used to prevent or treat a disease or disorder associated with Cx43 signaling. Signaling of Cx43 may be reduced by any suitable drugs to prevent cancer cell proliferation. Preferably, such substances would be an anti-Cx43 antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the Cx43 signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Compositions

Certain aspects include a composition, e.g., a pharmaceutical composition, containing one or a combination of monoclonal antibodies, or antigen-binding portion(s) thereof formulated with a pharmaceutically acceptable carrier. Such compositions may include one or a combination of (e.g., two or more different) antibodies, or immunoconjugates described herein. For example, a pharmaceutical composition of the invention can comprise a combination of antibodies that bind to different epitopes on the target antigen or that have complementary activities.

Pharmaceutical compositions of the invention also can be administered as combination therapy, i.e., combined with other agents. For example, the combination therapy can include an anti-hemichannel antibody combined with at least one other anti-cancer agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, or parenteral administration (e.g., by injection or infusion). Depending on the route of administration, the active compound, i.e., antibody, or immunoconjugate, may be coated in a material to protect the compound from the action of acids and other natural conditions that may inactivate the compound.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-hemichannel antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-hemichannel antibody results in a decrease in severity of disease symptoms, an increase in frequency and duration of disease symptom-free periods, or a prevention of impairment or disability due to the disease affliction. A therapeutically effective amount of a therapeutic compound or antibody can decrease tumor metastasis, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, or other parenteral routes of administration, for example by injection or infusion. The phrase "parenteral administration" as used herein means modes of administration other than enteral and topical administration, usually by injection, and includes, without limitation, intravenous, intramuscular, intraarterial, intraperitoneal, transtracheal, subcutaneous, subcuticular, intraarticular injection and infusion.

B. Combination Treatments

In certain embodiments, the compositions and methods of the present embodiments involve an antibody or an antibody fragment against Cx43 to inhibit its activity in cancer cell proliferation, in combination with a second or additional therapy. Such therapy can be applied in the treatment of any disease that is associated with Cx43-mediated cell proliferation. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

A/B/A B/A/B B/B/A A/A/B A/B/B B/A/A A/B/B/B B/A/B/B B/B/B/A B/B/A/B A/A/B/B

A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

[A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons a, (3, and y, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. KITS AND DIAGNOSTICS

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one Cx43 antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Anti-Cx43 Monoclonal Antibodies

Anti-Cx43 monoclonal antibodies were generated and clones were identified that produced Cx43-binding monoclonal antibodies. CDR sequences of both DNA and amino acids for all antibody sequences are shown in the tables below along with the correct pairing for each of the characterized antibodies.

TABLE 1

Pairing of heavy chain and light chain for two functional antibodies.

| Antibody Name | Heavy chain | Light chain |
|---|---|---|
| M1 (HmAb1) | M1H | M1K1 |
| M2 (HmAb2) | M1H | M1M7K |

TABLE 2

Sequence of antibody chains from the hybridomas.

| mAB | CDR-1 | CDR-2 | CDR-3 |
|---|---|---|---|
| M1H | ggctacaccttcaccagctactat (SEQ ID NO: 16) GYTFTSYY (SEQ ID NO: 19) | attaatcctagcaatggtggtact (SEQ ID NO: 17) INPSNGGT (SEQ ID NO: 20) | acaagagagggtaacccctactatactatgaactac (SEQ ID NO: 18) TREGNPYYTMNY (SEQ ID NO: 21) |
| M7H | ggctacatcttcaccacctactgg (SEQ ID NO: 22) GYIFITYW (SEQ ID NO: 25) | attagtcctagcaacggtcgttct (SEQ ID NO: 23) ISPSNGRS (SEQ ID NO: 26) | gcacgattcgacgaggggacttc (SEQ ID NO: 24) ARFDEGDF (SEQ ID NO: 27) |
| M1K1 | cagagtctgttaaacagtggaaatcaaaagacctac (SEQ ID NO: 28) QSLLNSGNQKTY (SEQ ID NO: 31) | ggggcatcc (SEQ ID NO: 29) GAS (SEQ ID NO: 32) | cagaatgatcatagttatccattcacg (SEQ ID NO: 30) QNDYSYPFT (SEQ ID NO: 33) |
| M1K2 | aaaagtgtcagtacatctggctatagttat (SEQ ID NO: 34) KSVSTSGYSY (SEQ ID NO: 37) | cttgtatcc (SEQ ID NO: 35) LVS (SEQ ID NO: 38) | cagcacattagggagcttacacg (SEQ ID NO: 36) QHIRELT (SEQ ID NO: 39) |
| M2K | aaaagtgtcagtacatctggctatagttat (SEQ ID NO: 40) KSVSTSGYSY (SEQ ID NO: 43) | cttgtatcc (SEQ ID NO: 41) LVS (SEQ ID NO: 44) | cagcacattagggagcttacacgt (SEQ ID NO: 42) QHIRELTR (SEQ ID NO: 45) |
| M1M7K | gagcctcttagaaagcgatggaaagacatat (SEQ ID NO: 46) QSLLESDGKTY (SEQ ID NO: 49) | ctggtgtct (SEQ ID NO: 47) LVS (SEQ ID NO: 50) | tggcaaggtacacattttccgtggacg (SEQ ID NO: 48) WQGTHFPWT (SEQ ID NO: 51) |

Cloned variable domains are shown in the charts below.
Chart 1. DNA Sequences:

>M1H
(SEQ ID NO: 52)
GAGGTCCAACTCCAGCAGCCTGGGGCTGAACTGGTGAAGCCTGGGGCTTCAGTGAAGTTGTC

CTGCAAGGCTTCTGGCTACACCTTCACCAGCTACTATATGTACTGGGTGAAGCAGAGGCCTG

GACAAGGCCTTGAGTGGATTGGGGGAATTAATCCTAGCAATGGTGGTACTAACTTCAATGAG

AAGTTCAAGAACAAGGCCACACTGACTGTAGACAAATCCTCCAGCACAGCCTACATGCAAC

TCAGCAGCCTGACATCTGAGGACTCTGCGGTCTATTACTGTACAAGAGAGGGTAACCCCTAC

TATACTATGAACTACTGGGGTCAAGGAACCTCAGTCACCGTCTCCTCA

>M7H
(SEQ ID NO: 53)
GAGGTCCAACTCCAGCAACCTGGGGCTGAACTGGTGAGGCCTGGGGCTTCAGTAATGCTGTC

CTGCAAGGCTTCTGGCTACATCTTCACCACCTACTGGATGCACTGGCTGAAGCAGAGGCCTG

GACAAGGCCTTGACTGGATTGGAGAGATTAGTCCTAGCAACGGTCGTTCTAATTACAATAAG

AAGTTCAAGAGCAAGGCCACACTGACTGTAGACAAATCCTCCAGCACAGCCTACATGCAAC

TCAGCAGCCTGACATCTGAGGACTCTGCGGTCTATTACTGTGCACGATTCGACGAGGGGGAC

TTCTGGGGCCAAGGCACCACTCTCATAGTCTCCTCA

>M1K1
(SEQ ID NO: 54)
GACATTGTGATGACGCAGTCTCCATCCTCCCTGAGTGTGTCAGCAGGAGAGAAGGTCACTAT

GAGCTGCAAGTCCAGTCAGAGTCTGTTAAACAGTGGAAATCAAAAGACCTACTTGGCCTGGT

ACCAGCAGAAACCAGGGCAGCCTCCTAAACTGTTGATCTACGGGGCATCCACTAGGGAATC

TGGGGTCCCTGATCGCTTCACAGGCAGTGGATCTGGAACCGATTTCACTCTTACCATCAGCA

GTGTGCAGGCTGAAGACCTGGCAGTTTATTACTGTCAGAATGATCATAGTTATCCATTCACG

TTCGGCTCGGGGACAAAGTTGGAAATAAAA

>M1K2
(SEQ ID NO: 55)
GACATTGTGTTGACACAGTCTCCTGCTTCCTTAGCTGTATCTCTGGGGCAGAGGGCCACCATC

TCATACAGGGCCAGCAAAAGTGTCAGTACATCTGGCTATAGTTATATGCACTGGAACCAACA

GAAACCAGGACAGCCACCCAGACTCCTCATCTATCTTGTATCCAACCTAGAATCTGGGGTCC

CTGCCAGGTTCAGTGGCAGTGGGTCTGGGACAGACTTCACCCTCAACATCCATCCTGTGGAG

GAGGAGGATGCTGCAACCTATTACTGTCAGCACATTAGGGAGCTTACACGTTCGGAGGGGG

GACCAAGCTGGAAATCAAAC

>M2K
(SEQ ID NO: 56)
GATATTGTGATGACCCAGTCTCCCGCTTCCTTAGCTGTATCTCTGGGGCAGAGGGCC

ACCATCTCATACAGGGCCAGCAAAAGTGTCAGTACATCTGGCTATAGTTATATGCACTGGA

ACCAACAGAAACCAGGACAGCCACCCAGACTCCTCATCTATCTTGTATCCAACCTAGAATCT

GGGGTCCCTGCCAGGTTCAGTGGCAGTGGGTCTGGGACAGACTTCACCCTCAACATCCATCC

TGTGGAGGAGGAGGATGCTGCAACCTATTACTGTCAGCACATTAGGGAGCTTACACGTTCGG

AGGGGGGGACCAAGCTGGAAATCAAA

>M1M7
(SEQ ID NO: 57)
KGACGTTGTGATGACCCAGACTCCACTCACTTTGTCGGTTACCATTGGACAACCAGCCTCCA

TCTCTTGCAAGTCAAGTCAGAGCCTCTTAGAAAGCGATGGAAAGACATATTTGAATTGGTTG

TTACAGAGGCCAGGCCAGTCTCCAAAGCGCCTAATCTATCTGGTGTCTAAACTGGACTCTGG

AGTCCCTGACAGGTTCACTGGCAGTGGATCAGGGACAGATTTCACACTGAAAATCAGCAGA

```
GTGGAGGCTGAGGATTTGGGAGTTTATTATTGCTGGCAAGGTACACATTTTCCGTGGA

CGTTCGGTGGAGGCACCAAGCTGGAAATCAAA
```

Chart 2. Amino Acid Sequences:

>M1H
(SEQ ID NO: 58)
EVQLQQPGAELVKPGASVKLSCKASGYTFTSYYMYWVKQRPGQGLEWIGGI

NPSNGGTNFNEKFKNKATLTVDKSSSTAYMQLSSLTSEDSAVYYCTREGNP

YYTMNYWGQGTSVTVSS

>M7H
(SEQ ID NO: 59)
EVQLQQPGAELVRPGASVMLSCKASGYIFTTYWMHWLKQRPGQGLDWIGEI

SPSNGRSNYNKKFKSKATLTVDKSSSTAYMQLSSLTSEDSAVYYCARFDEG

DFWGQGTTLIVS

>M1K1
(SEQ ID NO: 60)
DIVMTQSPSSLSVSAGEKVTMSCKSSQSLLNSGNQKTYLAWYQQKPGQPPK

WYGASTRSGVPDRFTGSGSGTDFTLTISSVQAEDLAVYYCQNDHSYPFTFG

SGTKLEIK

>M1K2
(SEQ ID NO: 61)
DIVLTQSPASLAVSLGQRATISYRASKSVSTSGYSYMHWNQQKPGQPPRLL

IYLVSNL ES GVPARF S GS GS GTDF TLNIHPVEEEDAATYYC QH

IRELTRS EGGP S WKSN

>M2-K
(SEQ ID NO: 62)
DIVMTQSPASLAVSLGQRATISYRASKSVSTSGYSYMHWNQQKPGQPPRLL

IYLVSNLESGVPARFSGSGSGTDFTLNIHPVEEEDAATYYCQHIRELTRSE

GGTKLEIK

>M1M7-K
(SEQ ID NO: 63)
DVVMTQTPLTLSVTIGQPASISCKSSQSLLESDGKTYLNWLLQRPGQSPKR

LIYLVSKLDSGVPDRFTGSGSGTDFTLKISRVEAEDLGVYYCWQGTHFPWT

FGGGTKLEIK

Example 2—Spinal Cord and Neuronal Injury (SCI) Therapeutic Use

Figure 1:
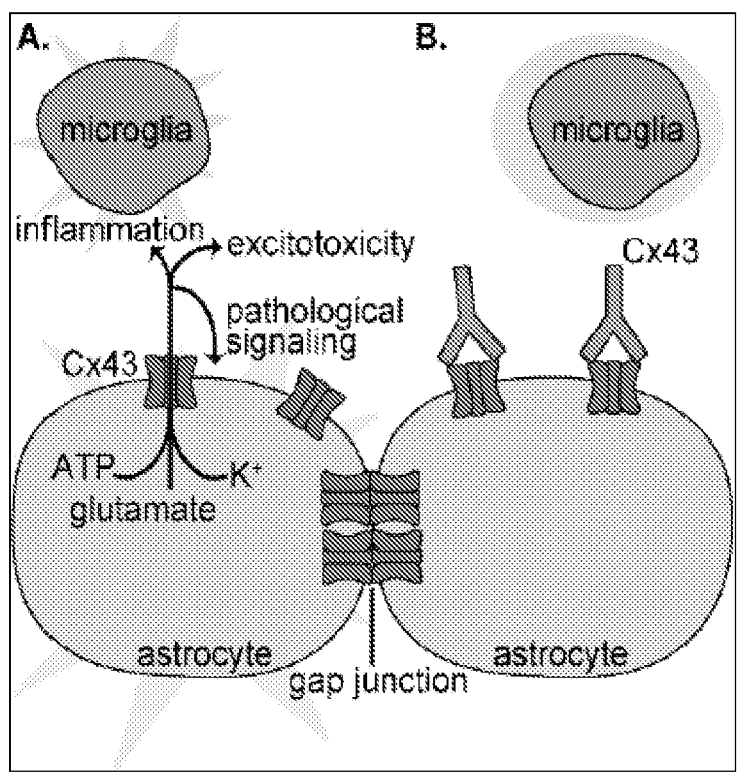
FIG. 1—Cx43 is normally localized into gap junctions between cells or as hemichannels on the plasma membrane. In side A) Pathological opening of Cx43 hemichannels result in propagation of secondary injury, activation of astro/microglia, and inflammation. Side B) illustrates the proposal that preventing pathological opening of Cx43 hemichannels prevents release of molecules, enabling astrocytes to act as caretaker cells and prevent further spread of secondary injury.

As illustrated in FIG. 1, Cx43 is normally localized into gap junctions between cells or as hemichannels on the plasma membrane. Pathological opening of Cx43 hemichannels result in propagation of secondary injury, activation of astro/microglia, and inflammation. It is proposed that preventing pathological opening of Cx43 hemichannels prevents release of molecules, enabling astrocytes to act as caretaker cells and prevent further spread of secondary injury.

Figure 2:
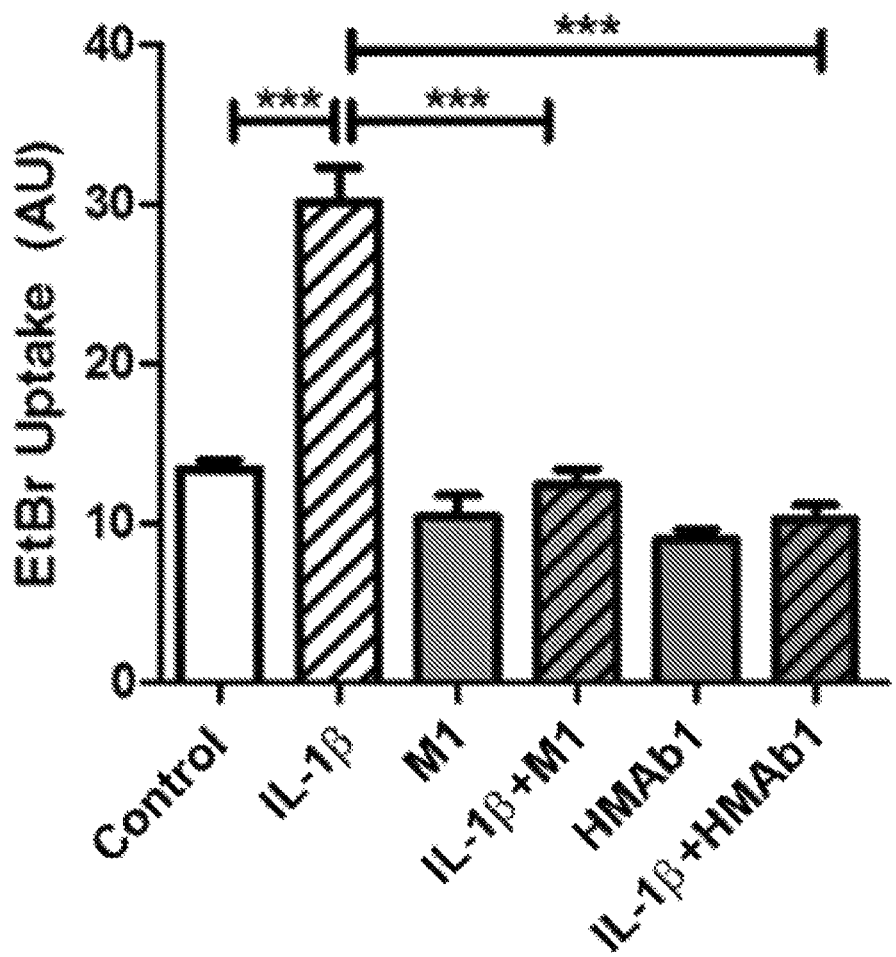
FIG. 2—The activation of Cx43 hemichannels by IL-1β in human primary astrocytes was inhibited by both Cx43 hemichannel blocking mouse monoclonal antibody (M1) and mouse-human chimeric antibody HMAb1 (these antibodies comprise the same murine variable domains and CDRs). The hemichannel activity was determined by ethidium bromide uptake.

The activation of Cx43 hemichannels by IL-10 in human primary astrocytes was inhibited by both Cx43 hemichannel blocking mouse monoclonal antibody (M1) and mouse-human chimeric antibody HMAb1. The hemichannel activity was determined by ethidium bromide uptake. The results are shown in FIG. 2.

Figures 3A, 3B, 3C, 3D, 3E, 3F, 3G:
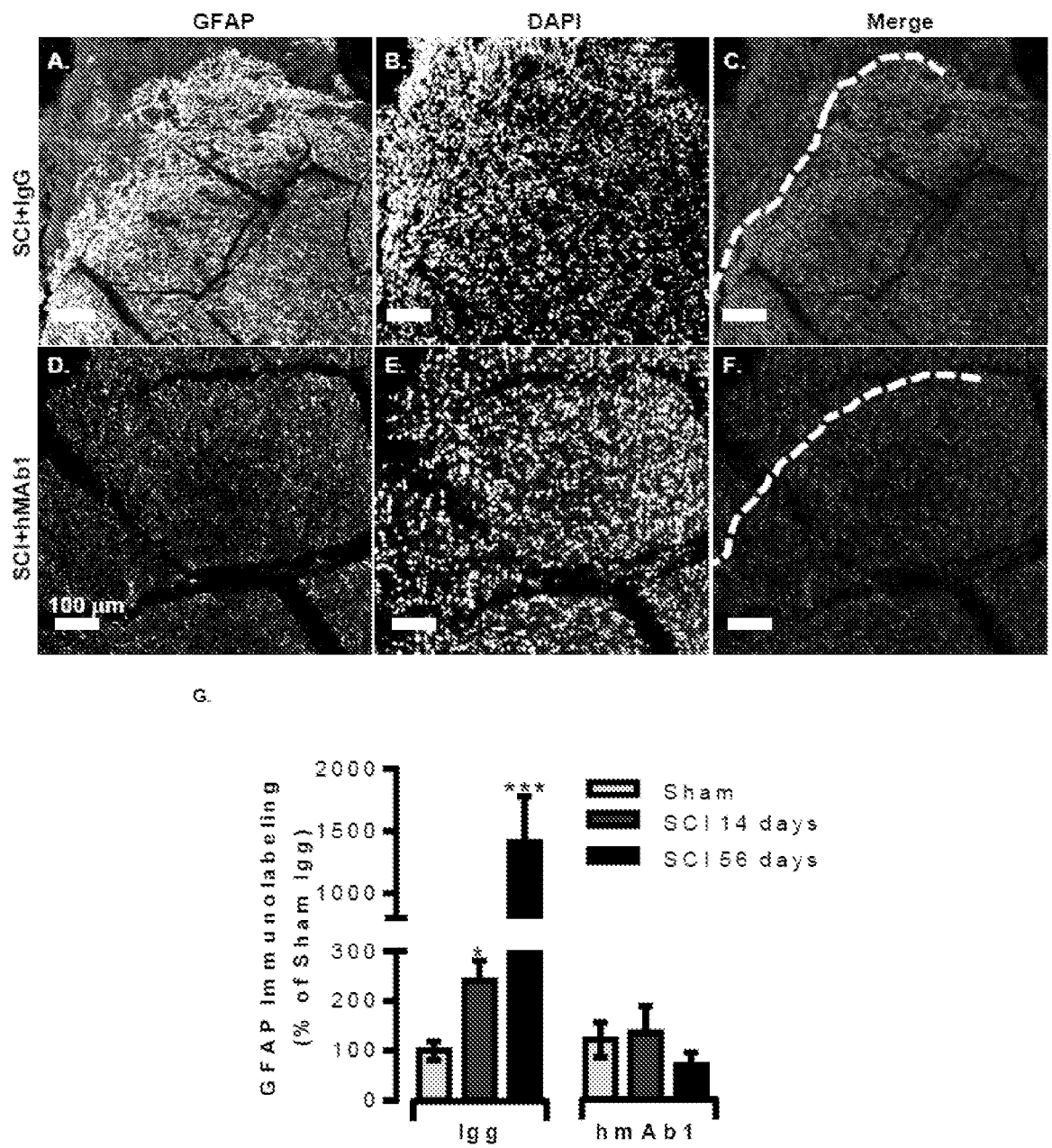
FIGS. 3A-3G—Mice were subjected to a single SCI and treated 30 minutes after injury with IP saline, control IgG, or HMAb1 (25 mg/kg). Glial scarring was measured at 14 and 56 days after injury. (A-F) Representative images of spinal cords in mice treated with (A-C) control IgG or (D-F)

Mice treated with HMAb1 had decreased glial scarring. Mice were subjected to a single SCI and treated 30 minutes after injury with IP saline, control Igg, or HMAb1 (25 mg/kg). Glial scarring was measured at 14 and 56 days after injury. Spinal cord tissue sections were subjected to immunohistochemistry for the astrocyte marker GFAP (red). Representative images of spinal cords in mice treated with the control IgG are shown in FIGS. 3A-C and those treated with HMAb1 are shown in FIGS. 3D-F. The lesion boundary is indicated with a dotted white line. GFAP immunolabeling was quantified as the mean intensity multiplied by area of positive stain in FIG. 3G. Results are expressed as a percentage of Sham surgery, IgG treated mice. Results are averages with SEM. *$p<0.05$, ***$p<0.001$ compared to Igg w/Tukey's HSD n=3-4.

Glial scarring was also reduced in mice treated with anti-Cx43 after SCI. Mice were subjected to SCI and treated with IgG or anti-Cx43 antibody (M1) at 30 minutes post injury. Two weeks after injury, tissue sections were analyzed for expression of the astrocyte marker GFAP. Representative images are shown in FIGS. 4A and 4B. The results are quantified in FIG. 4C.

Mice with SCI recover hind limb function after treatment with HMAb1 (FIGS. 5A-5B). Mice were subjected to a single SCI and treated 30 minutes after injury with IP saline, control IgG, or human-mouse chimeric anti-Cx43 antibody (HMAb1) (25 mg/kg).

Figures 6A, 6B, 6C, 6D, 6E, 6F, 6G:
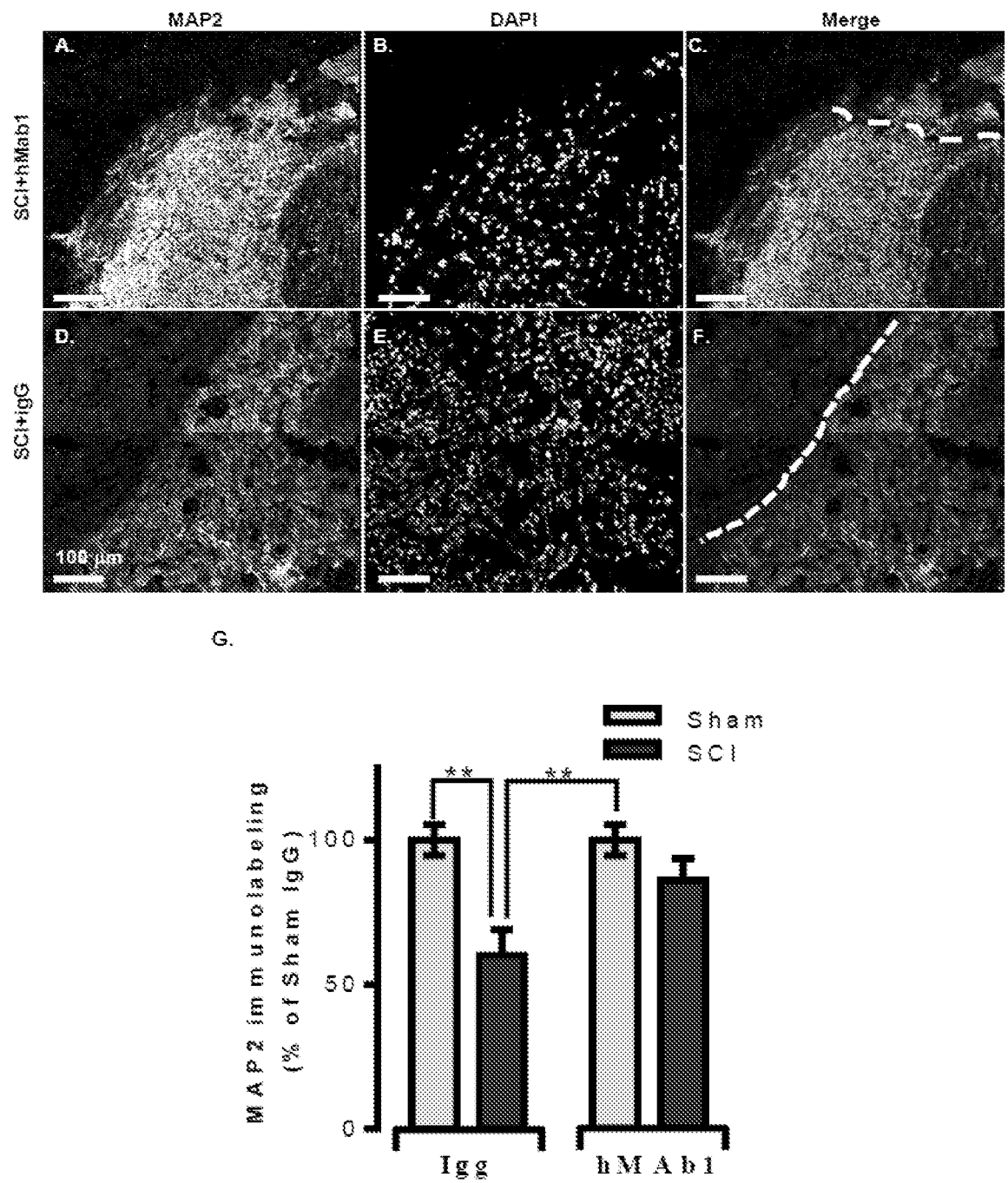

Mice treated with HMAb1 were found to have more neuronal dendrites in the perilesional area 14 days post SCI. As described above, mice were subjected to a single SCI and treated 30 minutes after injury with IP saline, control Igg, or HMAb1 (25 mg/kg). Neuronal dendrites were measured by immunolabeling against the neuronal marker MAP2. Immunohistochemistry representative images of spinal cords in mice treated with control IgG are shown in FIGS. 6A-C and those treated with HMAb1 are shown in 6D-F. The lesion boundary is indicated with a dotted white line. MAP2 immunolabeling was quantified as the mean intensity multiplied by area of positive stain, illustrated in FIG. 6G. Results are expressed as a percentage of Sham surgery, IgG treated mice.

Mice treated with HMAb1 also were observed to have more neuronal nuclei in the perilesional area 14 days post SCI. Mice were again subjected to a single SCI and treated 30 minutes after injury with IP saline, control IgG, or HMAb1 (25 mg/kg). Neuronal nuclei were measured by immunolabeling against the neuronal marker NeuN. Immunohistochemistry representative images of spinal cords in mice treated with control IgG are shown in FIGS. 7A-C and those treated with HMAb1 are shown in 7D-F. The lesion boundary is indicated with a dotted white line. NeuN immunolabeling was quantified as the mean intensity multiplied by area of positive stain, shown in FIG. 7G. Results are expressed as a percentage of Sham surgery, IgG treated mice.

Example 3—Diagnostic and Cancer Therapeutic Use

There are approximately 40,000 deaths from metastatic breast cancer annually in the United States. About 70-80% of patients with advanced breast cancer develop skelatal metastases. Bone metastases alone account for two-thirds of the cost of breast cancer treatment.

It was found that osteolytic tumor growth was augmented in osteocyte-specific Cx43 knockout mice. Py8119-Luc cells were injected into right tibias of control and cKO female mice. The left tibias were injected with PBS as controls. The tumor growth was recorded every week for 4 weeks by bioluminescence imaging and quantified (FIGS. 8A-8C).

MLO-Y4 osteocytes and primary mouse osteocytes were incubated with E2 (polyclonal), HMAb1 and HMAb2 antibody or carbenoxolone (CBX), a connexin channel blocker. Ethium bromide (EtBr) dye uptake assay was performed (FIGS. 9A-9B). It was found that Cx43 HMAb2 antibody activates hemichannels.

Additionally, Cx43(M1) antibody was delivered to osteocytes in vivo and found to block Evans blue uptake induced by tibial loading. Evans blue dye was injected into tail vein of WT, osteocyte-specific Cx43 KO. Mouse IgG or Cx43 (M1) mAb (25 mg/kg) was i.p. injected 2 hrs before dye injection. 30 min after dye injection, left tibias were mechanically loaded once for 10 min. Mice were sacrified and perfused with PBS. Tibias were isolated and fixed tibial bone tissue sections were prepared. The results are shown in FIGS. 10A-10C.

The inhibition of osteolytic tumor growth by HMAb2 was also observed. Py8119-Luc cells were injected into right tibias of female mice (FIG. 11A). The left tibias were injected with PBS as controls. HMAb2 at 25 mg/kg was i.p. injected either once or twice per week for four weeks. Saline was injected twice per week in control mice. The tumor growth was recorded every week for 4 weeks by bioluminescence imaging and quantified (FIG. 11B).

Example 4—Osteoarthritis Treatment

Primary chondrocytes isolated from mouse bone were immunostained with anti-Cx43 antibody against C-terminal domain (Total) in permeable cells and Cx43E2 antibody in non-permeable cells (FIG. 12). Cx43 expression was observed on the cell surface of the primary chondrocytes.

In another study, primary chondrocytes isolated from mouse bone were pre-treated with carbenoxolone (connexin channel blocker) or HMAb1 antibody and then treated with or without IL-1β. Ethidium bromide dye uptake assay was performed to determine hemichannel activity (FIG. 13). It was observed that HMAb1 antibody inhibits hemichannel opening by IL-1β in primary chondrocytes.

As in the above example, Evans blue uptake induced by tibial loading was blocked by Cx43 hemichannel blocking antibody in vivo. Evans blue dye was injected into tail vein of WT mice. Cx43(M1) mAb (25 mg/kg) was i.p. injected 2 hrs before dye injection. 30 min after dye injection, left tibias were mechanically loaded once for 10 min. Dye uptake was measured by Evans blue (EB) fluorescence and quantified (FIG. 14).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of treating an osteolytic tumor in a subject, the method comprising administering to the subject an effective amount of an antibody that binds to a connexin 43 (Cx43) hemichannel and enhances channel opening, wherein the antibody comprises:
   (a) a first VH CDR identical to SEQ ID NO: 19;
   (b) a second VH CDR identical to SEQ ID NO: 20;
   (c) a third VH CDR identical to SEQ ID NO: 21;
   (d) a first VL CDR identical to SEQ ID NO: 49;
   (e) a second VL CDR identical to SEQ ID NO: 50; and
   (f) a third VL CDR identical to SEQ ID NO: 51.

2. The method of claim 1, wherein the antibody is administered in a pharmaceutically acceptable composition.

3. The method of claim 1, wherein the antibody is administered intravenously, intradermally, intratumorally, intramuscularly, intraperitoneally, subcutaneously, or locally.

4. The method of claim 1, wherein the antibody is a humanized antibody.

5. The method of claim 1, wherein the antibody comprises a VH amino acid sequence according to SEQ ID NO: 58 and/or a VL amino acid sequence according to SEQ ID NO: 63.

6. A method of treating spinal cord injury in a subject, the method comprising administering to the subject an effective amount of an antibody that binds to a connexin 43 (Cx43) hemichannel and inhibits channel opening, wherein the antibody comprises:
   (a) a first VH CDR identical to SEQ ID NO: 19;
   (b) a second VH CDR identical to SEQ ID NO: 20;
   (c) a third VH CDR identical to SEQ ID NO: 21;
   (d) a first VL, CDR identical to SEQ ID NO: 31;
   (e) a second VL, CDR identical to SEQ ID NO: 32; and
   (f) a third VL, CDR identical to SEQ ID NO: 33.

7. The method of claim 6, wherein the antibody is administered in a pharmaceutically acceptable composition.

8. The method of claim 6, wherein the antibody is administered intravenously, intradermally, intratumorally, intramuscularly, intraperitoneally, subcutaneously, or locally.

9. The method of claim 6, wherein the antibody is a humanized antibody.

10. The method of claim 6, wherein the antibody comprises a VH amino acid sequence according to SEQ ID NO: 58 and/or a VL amino acid sequence according to SEQ ID NO: 60.

* * * * *

SEQUENCE LISTING

```
<160> NUMBER OF SEQ ID NOS: 63

<210> SEQ ID NO 1
<211> LENGTH: 384
<212> TYPE: DNA
<213> ORGANISM: Mus musculus

<400> SEQUENCE: 1
gaggttcagc tggagcagcc tggggctgaa ctggtgaagc ctggggcttc agtgaagttg      60
tcctgcaagg cttctggcta caccttcacc agctactata tgtactgggt gaagcagagg     120
cctggacaag gccttgagtg gattggggga attaatccta gcaatggtgg tactaacttc     180
aatgagaagt tcaagaacaa ggccacactg actgtagaca aatcctccag cacagcctac     240
atgcaactca gcagcctgac atctgaggac tctgcggtct attactgtac aagagagggt     300
aacccctact atactatgaa ctactggggt caaggaacct cagtcaccgt ctcctcagcc     360
aaaacgacac ccccatctgt ctat                                            384

<210> SEQ ID NO 2
<211> LENGTH: 128
<212> TYPE: PRT
<213> ORGANISM: Mus musculus

<400> SEQUENCE: 2

Glu Val Gln Leu Glu Gln Pro Gly Ala Glu Leu Val Lys Pro Gly Ala
1               5                   10                  15
```

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Thr Arg Glu Gly Asn Pro Tyr Tyr Thr Met Asn Tyr Trp Gly Gln Gly
            100                 105                 110

Thr Ser Val Thr Val Ser Ser Ala Lys Thr Thr Pro Pro Ser Val Tyr
            115                 120                 125

<210> SEQ ID NO 3
<211> LENGTH: 324
<212> TYPE: DNA
<213> ORGANISM: Mus musculus

<400> SEQUENCE: 3
gatattgtga tgacacagac tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaa                                            324

<210> SEQ ID NO 4
<211> LENGTH: 108
<212> TYPE: PRT
<213> ORGANISM: Mus musculus

<400> SEQUENCE: 4

Asp Ile Val Met Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
            85                  90                  95

Glu Leu Thr Arg Ser Glu Gly Gly Pro Ser Trp Lys
            100                 105

<210> SEQ ID NO 5
<211> LENGTH: 384
<212> TYPE: DNA
<213> ORGANISM: Mus musculus

<400> SEQUENCE: 5

```
gaggttcagc tggagcagcc tggggctgaa ctggtgaagc ctggggcttc agtgaagttg    60
tcctgcaagg cttctggcta caccttcacc agctactata tgtactgggt gaagcagagg   120
cctggacaag gccttgagtg gattggggga attaatccta gcaatggtgg tactaacttc   180
aatgagaagt tcaagaacaa ggccacactg actgtagaca atcctccag cacagcctac    240 atgcaactca gcagcctgac atctgaggac tctgcggtct attactgtac aagagagggt   300 aaccccctact atactatgaa ctactgggggt caaggaacct cagtcaccgt ctcctcagcc  360
aaaacgacac ccccatctgt ctat                                          384
```

<210> SEQ ID NO 6
<211> LENGTH: 128
<212> TYPE: PRT
<213> ORGANISM: Mus musculus

<400> SEQUENCE: 6

```
Glu Val Gln Leu Glu Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Ser Val Thr Val Ser Ser Ala Lys Thr Thr Pro Pro Ser Val Tyr
        115                 120                 125
```

<210> SEQ ID NO 7
<211> LENGTH: 375
<212> TYPE: DNA
<213> ORGANISM: Mus musculus

<400> SEQUENCE: 7

```
gatattgtga tgacccagac tccatcctcc ctgagtgtgt cagcaggaga gaaggtcact    60
atgagctgca gtccagtca gagtctgtta acagtggaa atcaaaagac ctacttggcc    120
tggtaccagc agaaaccagg gcagcctcct aaactgttga tctacggggc atccactagg   180
gaatctgggg tccctgatcg cttcacaggc agtggatctg gaaccgattt cactcttacc   240
atcagcagtg tgcaggctga agacctggca gtttattact gtcagaatga tcatagttat   300
ccattcacgt tcggctcggg gacaaagttg gaaataaaac gggctgatgc tgcaccaact   360
gtatccgcat gcacc                                                    375
```

<210> SEQ ID NO 8
<211> LENGTH: 122
<212> TYPE: PRT
<213> ORGANISM: Mus musculus

<400> SEQUENCE: 8

```
Asp Ile Val Met Thr Gln Thr Pro Ser Ser Leu Ser Val Ser Ala Gly
1               5                   10                  15
```

-continued

Glu Lys Val Thr Met Ser Cys Lys Ser Ser Gln Ser Leu Leu Asn Ser
            20                  25                  30

Gly Asn Gln Lys Thr Tyr Leu Ala Trp Tyr Gln Lys Pro Gly Gln
        35                  40                  45

Pro Pro Lys Leu Leu Ile Tyr Gly Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
            100                 105                 110

Lys Arg Ala Asp Ala Ala Pro Thr Val Ser
        115                 120

<210> SEQ ID NO 9
<211> LENGTH: 405
<212> TYPE: DNA
<213> ORGANISM: Mus musculus

<400> SEQUENCE: 9
ctggagcagc ctggggctga actggtgagg cctggggctt cagtaatgct gtcctgcaag     60
gcttctggct acatcttcac cacctactgg atgcactggc tgaagcagag gcctggacaa    120
ggccttgact ggattggaga gattagtcct agcaacggtc gttctaatta caataagaag    180
ttcaagagca aggccacact gactgtagac aaatcctcca gcacagccta catgcaactc    240
agcagcctga catctgagga ctctgcggtc tattactgtg cacgattcga cgaggggggac    300
ttctggggcc aaggcaccac tctcatagtc tcctcagcca aaacaacagc cccatcggtc    360
tatccactgg cccctgtgtg tggagataca actggctcct cggtg                    405

<210> SEQ ID NO 10
<211> LENGTH: 135
<212> TYPE: PRT
<213> ORGANISM: Mus musculus

<400> SEQUENCE: 10

Leu Glu Gln Pro Gly Ala Glu Leu Val Arg Pro Gly Ala Ser Val Met
1               5                   10                  15

Leu Ser Cys Lys Ala Ser Gly Tyr Ile Phe Thr Thr Tyr Trp Met His
            20                  25                  30

Trp Leu Lys Gln Arg Pro Gly Gln Gly Leu Asp Trp Ile Gly Glu Ile
        35                  40                  45

Ser Pro Ser Asn Gly Arg Ser Asn Tyr Asn Lys Lys Phe Lys Ser Lys
50                  55                  60

Ala Thr Leu Thr Val Asp Lys Ser Ser Ser Thr Ala Tyr Met Gln Leu
65                  70                  75                  80

Ser Ser Leu Thr Ser Glu Asp Ser Ala Val Tyr Tyr Cys Ala Arg Phe
                85                  90                  95

Asp Glu Gly Asp Phe Trp Gly Gln Gly Thr Thr Leu Ile Val Ser Ser
            100                 105                 110

Ala Lys Thr Thr Ala Pro Ser Val Tyr Pro Leu Ala Pro Val Cys Gly
        115                 120                 125

Asp Thr Thr Gly Ser Ser Val
        130                 135

<210> SEQ ID NO 11
<211> LENGTH: 324
<212> TYPE: DNA
<213> ORGANISM: Mus musculus

<400> SEQUENCE: 11

```
gatattgtga tgacacagac tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttacacgt   300
tcggaggggg gaccaagctg gaaa                                           324
```

<210> SEQ ID NO 12
<211> LENGTH: 108
<212> TYPE: PRT
<213> ORGANISM: Mus musculus

<400> SEQUENCE: 12

Asp Ile Val Met Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Phe Leu Ser Arg Pro Thr Glu Lys Thr Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic construct

<400> SEQUENCE: 14

Lys Arg Asp Pro Cys Pro His Gln Val Asp
1               5                   10

<210> SEQ ID NO 15
<211> LENGTH: 9
<212> TYPE: PRT
<213> ORGANISM: Artificial Sequence

```
<220> FEATURE:
<223> OTHER INFORMATION: Synthetic peptide

<400> SEQUENCE: 15

Leu Ser Ala Val Tyr Thr Cys Lys Arg
1               5

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
ggctacacct tcaccagcta ctat                                              24

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
attaatccta gcaatggtgg tact                                              24

<210> SEQ ID NO 18
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 18
acaagagagg gtaacccta ctatactatg aactac                                  36

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Gly Tyr Thr Phe Thr Ser Tyr Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Ile Asn Pro Ser Asn Gly Gly Thr
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21
```

Thr Arg Glu Gly Asn Pro Tyr Tyr Thr Met Asn Tyr
1               5                   10

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
ggctacatct tcaccaccta ctgg                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
attagtccta gcaacggtcg ttct                                              24

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gcacgattcg acgaggggga cttc                                              24

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Gly Tyr Ile Phe Thr Thr Tyr Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Ile Ser Pro Ser Asn Gly Arg Ser
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Ala Arg Phe Asp Glu Gly Asp Phe
1               5

```
<210> SEQ ID NO 28
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 28
cagagtctgt taaacagtgg aaatcaaaag acctac                                36

<210> SEQ ID NO 29
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 29 ggggcatcc                                                               9

<210> SEQ ID NO 30
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 30
cagaatgatc atagttatcc attcacg                                          27

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

Gln Ser Leu Leu Asn Ser Gly Asn Gln Lys Thr Tyr
1               5                   10

<210> SEQ ID NO 32
<211> LENGTH: 3
<212> TYPE: PRT
<213> ORGANISM: Artificial Sequence
<220> FEATURE:
<223> OTHER INFORMATION: Synthetic peptide

<400> SEQUENCE: 32

Gly Ala Ser
1

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Gln Asn Asp His Ser Tyr Pro Phe Thr
1               5

<210> SEQ ID NO 34
<211> LENGTH: 30
<212> TYPE: DNA
```

<210> SEQ ID NO 34
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 34
aaaagtgtca gtacatctgg ctatagttat                                30

<210> SEQ ID NO 35
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 35 cttgtatcc                                                        9

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
cagcacatta gggagcttac acg                                        23

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide

<400> SEQUENCE: 37

Lys Ser Val Ser Thr Ser Gly Tyr Ser Tyr
1               5                   10

<210> SEQ ID NO 38
<211> LENGTH: 3
<212> TYPE: PRT
<213> ORGANISM: Artificial Sequence
<220> FEATURE:
<223> OTHER INFORMATION: Synthetic peptide

<400> SEQUENCE: 38

Leu Val Ser
1

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Gln His Ile Arg Glu Leu Thr
1               5

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide

```
<400> SEQUENCE: 40
aaaagtgtca gtacatctgg ctatagttat                                      30

<210> SEQ ID NO 41
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 41 cttgtatcc                                                              9

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 42
cagcacatta gggagcttac acgt                                            24

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Lys Ser Val Ser Thr Ser Gly Tyr Ser Tyr
1               5                   10

<210> SEQ ID NO 44
<211> LENGTH: 3
<212> TYPE: PRT
<213> ORGANISM: Artificial Sequence
<220> FEATURE:
<223> OTHER INFORMATION: Synthetic peptide

<400> SEQUENCE: 44

Leu Val Ser
1

<210> SEQ ID NO 45
<211> LENGTH: 8
<212> TYPE: PRT
<213> ORGANISM: Artificial Sequence
<220> FEATURE:
<223> OTHER INFORMATION: Synthetic peptide

<400> SEQUENCE: 45

Gln His Ile Arg Glu Leu Thr Arg
1               5

<210> SEQ ID NO 46
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 46
gagcctctta gaaagcgatg gaaagacata t                                    31
```

<210> SEQ ID NO 47
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 47 ctggtgtct                                                              9

<210> SEQ ID NO 48
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 48
tggcaaggta cacattttcc gtggacg                                         27

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide

<400> SEQUENCE: 49

Gln Ser Leu Leu Glu Ser Asp Gly Lys Thr Tyr
1               5                   10

<210> SEQ ID NO 50
<211> LENGTH: 3
<212> TYPE: PRT
<213> ORGANISM: Artificial Sequence
<220> FEATURE:
<223> OTHER INFORMATION: Synthetic peptide

<400> SEQUENCE: 50

Leu Val Ser
1

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Trp Gln Gly Thr His Phe Pro Trp Thr
1               5

<210> SEQ ID NO 52
<211> LENGTH: 357
<212> TYPE: DNA
<213> ORGANISM: Artificial Sequence
<220> FEATURE:
<223> OTHER INFORMATION: Synthetic oligonucleotide

<400> SEQUENCE: 52
gaggtccaac tccagcagcc tggggctgaa ctggtgaagc ctggggcttc agtgaagttg      60
tcctgcaagg cttctggcta caccttcacc agctactata tgtactgggt gaagcagagg     120
cctggacaag gccttgagtg gattggggga attaatccta gcaatggtgg tactaacttc     180

| | |
|---|---|
| aatgagaagt tcaagaacaa ggccacactg actgtagaca aatcctccag cacagcctac | 240 |
| atgcaactca gcagcctgac atctgaggac tctgcggtct attactgtac aagagagggt | 300 |
| aacccctact atactatgaa ctactggggt caaggaacct cagtcaccgt ctcctca | 357 |

```
<210> SEQ ID NO 53
<211> LENGTH: 345
<212> TYPE: DNA
<213> ORGANISM: Artificial Sequence
<220> FEATURE:
<223> OTHER INFORMATION: Synthetic oligonucleotide

<400> SEQUENCE: 53
```

| | |
|---|---|
| gaggtccaac tccagcaacc tggggctgaa ctggtgaggc ctggggcttc agtaatgctg | 60 |
| tcctgcaagg cttctggcta catcttcacc acctactgga tgcactggct gaagcagagg | 120 |
| cctggacaag gccttgactg gattggagag attagtccta gcaacggtcg ttctaattac | 180 |
| aataagaagt tcaagagcaa ggccacactg actgtagaca aatcctccag cacagcctac | 240 |
| atgcaactca gcagcctgac atctgaggac tctgcggtct attactgtgc acgattcgac | 300 |
| gaggggggact tctggggcca aggcaccact ctcatagtct cctca | 345 |

```
<210> SEQ ID NO 54
<211> LENGTH: 339
<212> TYPE: DNA
<213> ORGANISM: Artificial Sequence
<220> FEATURE:
<223> OTHER INFORMATION: Synthetic oligonucleotide

<400> SEQUENCE: 54
```

| | |
|---|---|
| gacattgtga tgacgcagtc tccatcctcc ctgagtgtgt cagcaggaga gaaggtcact | 60 |
| atgagctgca gtccagtca gagtctgtta acagtggaa atcaaaagac ctacttggcc | 120 |
| tggtaccagc agaaaccagg gcagcctcct aaactgttga tctacggggc atccactagg | 180 |
| gaatctgggg tccctgatcg cttcacaggc agtggatctg gaaccgattt cactcttacc | 240 |
| atcagcagtg tgcaggctga agacctggca gtttattact gtcagaatga tcatagttat | 300 |
| ccattcacgt tcggctcggg gacaaagttg gaaataaaa | 339 |

```
<210> SEQ ID NO 55
<211> LENGTH: 330
<212> TYPE: DNA
<213> ORGANISM: Artificial Sequence
<220> FEATURE:
<223> OTHER INFORMATION: Synthetic oligonucleotide

<400> SEQUENCE: 55
```

| | |
|---|---|
| gacattgtgt tgacacagtc tcctgcttcc ttagctgtat ctctggggca gagggccacc | 60 |
| atctcataca gggccagcaa aagtgtcagt acatctggct atagttatat gcactggaac | 120 |
| caacagaaac caggacagcc acccagactc ctcatctatc ttgtatccaa cctagaatct | 180 |
| ggggtccctg ccaggttcag tggcagtggg tctgggacag acttcaccct caacatccat | 240 |
| cctgtggagg aggaggatgc tgcaacctat tactgtcagc acattaggga gcttacacgt | 300 |
| tcggaggggg gaccaagctg gaaatcaaac | 330 |

```
<210> SEQ ID NO 56
<211> LENGTH: 330
<212> TYPE: DNA
<213> ORGANISM: Artificial Sequence
<220> FEATURE:
<223> OTHER INFORMATION: Synthetic oligonucleotide
```

<400> SEQUENCE: 56

```
gatattgtga tgacccagtc tcccgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttacacgt   300
tcggagggg ggaccaagct ggaaatcaaa                                      330
```

<210> SEQ ID NO 57
<211> LENGTH: 337
<212> TYPE: DNA
<213> ORGANISM: Artificial Sequence
<220> FEATURE:
<223> OTHER INFORMATION: Synthetic oligonucleotide

<400> SEQUENCE: 57

```
kgacgttgtg atgacccaga ctccactcac tttgtcggtt accattggac aaccagcctc    60
catctcttgc aagtcaagtc agagcctctt agaaagcgat ggaaagacat atttgaattg   120
gttgttacag aggccaggcc agtctccaaa gcgcctaatc tatctggtgt ctaaactgga   180
ctctggagtc cctgacaggt tcactggcag tggatcaggg acagatttca cactgaaaat   240
cagcagagtg gaggctgagg atttgggagt ttattattgc tggcaaggta cacattttcc   300
gtggacgttc ggtggaggca ccaagctgga aatcaaa                             337
```

<210> SEQ ID NO 58
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 58

```
Glu Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
            20                  25                  30
Tyr Met Tyr Trp Val Lys Gln Arg Pro Gly Gln Gly Leu Glu Trp Ile
        35                  40                  45
Gly Gly Ile Asn Pro Ser Asn Gly Gly Thr Asn Phe Asn Glu Lys Phe
    50                  55                  60
Lys Asn Lys Ala Thr Leu Thr Val Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Thr Arg Glu Gly Asn Pro Tyr Tyr Thr Met Asn Tyr Trp Gly Gln Gly
            100                 105                 110
Thr Ser Val Thr Val Ser Ser
        115
```

<210> SEQ ID NO 59
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 59

Glu Val Gln Leu Gln Gln Pro Gly Ala Glu Leu Val Arg Pro Gly Ala
1               5                   10                  15

Ser Val Met Leu Ser Cys Lys Ala Ser Gly Tyr Ile Phe Thr Thr Tyr
            20                  25                  30

Trp Met His Trp Leu Lys Gln Arg Pro Gly Gln Gly Leu Asp Trp Ile
        35                  40                  45

Gly Glu Ile Ser Pro Ser Asn Gly Arg Ser Asn Tyr Asn Lys Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Phe Asp Glu Gly Asp Phe Trp Gly Gln Gly Thr Thr Leu Ile
            100                 105                 110

Val Ser Ser
        115

<210> SEQ ID NO 60
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 60

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Thr Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
            100                 105                 110

Lys

<210> SEQ ID NO 61
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 61

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala

```
                    50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                    85                  90                  95

Glu Leu Thr Arg Ser Glu Gly Gly Pro Ser Trp Lys Ser Asn
                100                 105                 110

<210> SEQ ID NO 62
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 62

Asp Ile Val Met Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
                 20                  25                  30

Gly Tyr Ser Tyr Met His Trp Asn Gln Gln Lys Pro Gly Gln Pro Pro
                 35                  40                  45

Arg Leu Leu Ile Tyr Leu Val Ser Asn Leu Glu Ser Gly Val Pro Ala
             50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                    85                  90                  95

Glu Leu Thr Arg Ser Glu Gly Gly Thr Lys Leu Glu Ile Lys
                100                 105                 110

<210> SEQ ID NO 63
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 63

Asp Val Val Met Thr Gln Thr Pro Leu Thr Leu Ser Val Thr Ile Gly
  1               5                  10                  15

Gln Pro Ala Ser Ile Ser Cys Lys Ser Ser Gln Ser Leu Leu Glu Ser
                 20                  25                  30

Asp Gly Lys Thr Tyr Leu Asn Trp Leu Leu Gln Arg Pro Gly Gln Ser
                 35                  40                  45

Pro Lys Arg Leu Ile Tyr Leu Val Ser Lys Leu Asp Ser Gly Val Pro
             50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                    85                  90                  95

Thr His Phe Pro Trp Thr Phe Gly Gly Gly Thr Lys Leu Glu Ile Lys
                100                 105                 110
```